(12) United States Patent
Maaskamp et al.

(10) Patent No.: US 10,799,690 B2
(45) Date of Patent: Oct. 13, 2020

(54) APPLICATOR FOR DISPENSING A MEDICINAL SUBSTANCE AND METHODS ASSOCIATED THEREWITH

(71) Applicants: Armand Maaskamp, Napa, CA (US); Ryan Maaskamp, San Francisco, CA (US); Irwin R. Berman, St. Simons Island, GA (US); Gervasio Salgado, Marbella (ES); Richard D. Gillespie, III, Athens, TX (US)

(72) Inventors: Armand Maaskamp, Napa, CA (US); Ryan Maaskamp, San Francisco, CA (US); Irwin R. Berman, St. Simons Island, GA (US); Gervasio Salgado, Marbella (ES); Richard D. Gillespie, III, Athens, TX (US)

(73) Assignee: SYRINGE LLC, Napa, CA (US)

( * ) Notice: Subject to any disclaimer, the term of this patent is extended or adjusted under 35 U.S.C. 154(b) by 145 days.

(21) Appl. No.: 14/756,523

(22) Filed: Sep. 14, 2015

(65) Prior Publication Data
US 2017/0072174 A1 Mar. 16, 2017
US 2017/0209679 A9 Jul. 27, 2017

Related U.S. Application Data

(63) Continuation of application No. 13/573,394, filed on Sep. 13, 2012, now Pat. No. 9,132,262.

(51) Int. Cl.
*A61M 31/00* (2006.01)
*A61M 5/32* (2006.01)

(52) U.S. Cl.
CPC ........ *A61M 31/007* (2013.01); *A61M 5/3291* (2013.01)

(58) Field of Classification Search
CPC ... A61M 31/007; A61M 5/329; A61M 5/3291
See application file for complete search history.

(56) References Cited

U.S. PATENT DOCUMENTS

| | | | | |
|---|---|---|---|---|
| 3,109,427 A * | 11/1963 | Davidson | ............... | A61M 31/00 222/575 |
| 3,536,411 A * | 10/1970 | Eisert | ..................... | B43M 11/06 401/176 |
| 3,667,461 A * | 6/1972 | Zamarra | .............. | A61M 3/0262 604/212 |
| 3,802,435 A * | 4/1974 | Claasen | ................... | A61M 3/00 604/200 |
| 4,906,239 A * | 3/1990 | Bruhl | ..................... | A61M 31/00 604/104 |
| 7,125,394 B2 * | 10/2006 | Berman | ................ | A61M 31/00 604/15 |
| 7,141,036 B2 * | 11/2006 | Berman | ................ | A61M 31/00 604/15 |

(Continued)

*Primary Examiner* — Andrew M Gilbert
(74) *Attorney, Agent, or Firm* — J. Bruce Hoofnagle

(57) ABSTRACT

An applicator 270 includes a stem 174 having an axially-formed slot delivery passage 200. A slot 350 is formed transaxially through the stem 174 and is in communication with the slot delivery passage 200. An extended side wall 350*b* is formed on one side of the slot 350. A flat surface 354, which is formed in the stem 174, is spaced and extends angularly away from an opposite side of the slot 176 and from the extended side wall 350*b* to provide for direct and lateral dispensing of a cream 280 onto a tissue 242 of a patient.

18 Claims, 16 Drawing Sheets

(56) References Cited

U.S. PATENT DOCUMENTS

| | | |
|---|---|---|
| 8,845,596 B2 | 9/2014 | Berman et al. |
| 8,986,312 B2 * | 3/2015 | Georgy .............. A61B 17/8811 606/92 |
| 9,132,262 B2 * | 9/2015 | Berman ................ A61M 31/00 |
| 2008/0021463 A1 * | 1/2008 | Georgy .............. A61B 17/8811 606/262 |
| 2008/0300575 A1 * | 12/2008 | Cleator ................ A61M 31/00 604/514 |
| 2010/0211021 A1 * | 8/2010 | Wong ................... A61M 39/24 604/247 |

\* cited by examiner

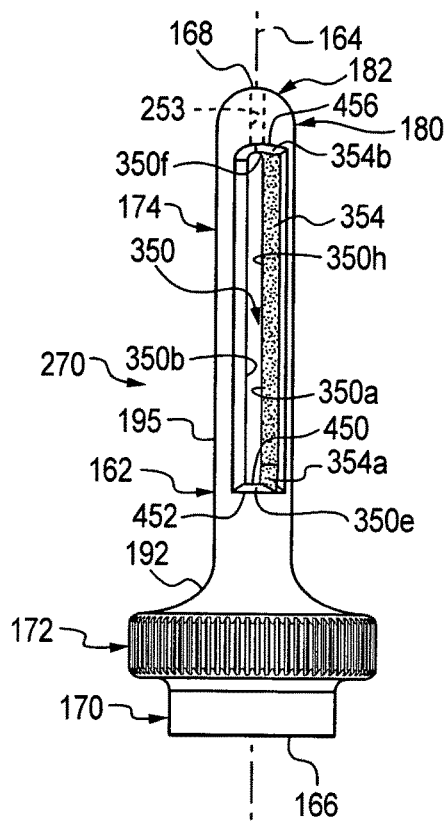
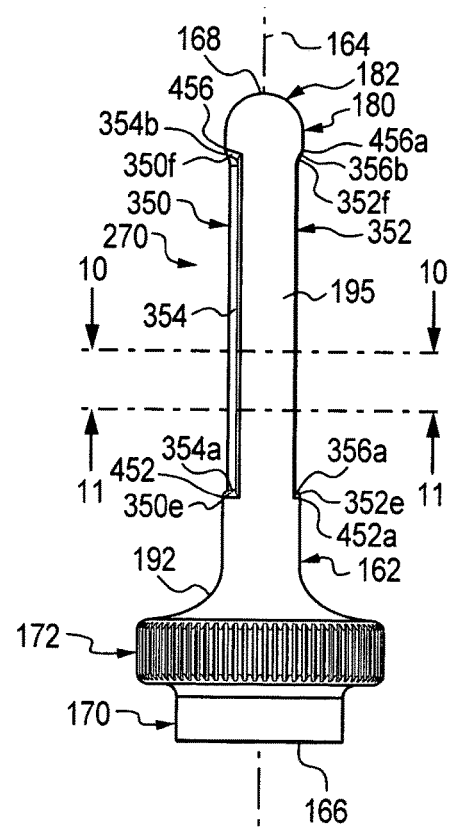
FIG. 7
FIG. 8

APPLICATOR FOR DISPENSING A MEDICINAL SUBSTANCE AND METHODS ASSOCIATED THEREWITH

This is a continuation application of U.S. application Ser. No. 13/573,394, filed on Sep. 13, 2012, and issued on Sep. 15, 2015, as U.S. Pat. No. 9,132,262 which is incorporated herein by reference thereto.

BACKGROUND OF THE INVENTION

This invention relates to an applicator for dispensing a medicinal substance, and to methods associated therewith. This invention particularly relates to an applicator for readily dispensing a medicinal substance such as, for example, medicinal cream, compound, or the like, from the applicator, and to methods of dispensing a medicinal substance.

Frequently, various medical conditions exist within affected areas of openings of the human body, such as, for example, (1) natural openings of the anatomy of the human body including, but not limited to, the vaginal opening and the anal opening, and (2) non-natural openings such as surgically-formed openings, and/or openings resulting from injury. All of the above-noted openings are hereinafter referred to as "body openings." These medical conditions can be treated with medicinal creams and other substances of similar consistency. Frequently, such creams are prescribed by physicians, and are to be applied to tissue within the body openings over a period of time.

Because of the necessity for frequent applications of the cream to the affected areas, it is beneficial and economical for the patient to self-administer the medicinal cream. However, the cream may be applied by caregivers other than the patient.

In the past, techniques and devices have been developed to facilitate the dispensing of the cream generally within the body openings, but have tended not to be formed with structure which dispenses an ample amount of the cream onto the affected areas for a most effective treatment.

Thus, there is a need for a cream-delivery device, such as an applicator or a tip (both hereinafter referred to as "the applicator"), which facilitates the dispensing of an ample amount of medicinal cream onto tissue of the affected areas to be treated. Also, there is a need for a cream-delivery device, such as the applicator, which facilitates extension of the dispensing of the medicinal cream axially beyond a through slot of the applicator.

SUMMARY OF THE INVENTION

It is, therefore, an object of this invention to provide an applicator which facilitates the dispensing of an ample amount of a substance onto tissue surfaces to be treated.

Another object of this invention is to provide an applicator which facilitates extension of the dispensing of a substance axially beyond a through slot of the applicator.

With these and other objects in mind, this invention contemplates an applicator for dispensing a substance therethrough, which includes a body formed (1) about an axis which extends from a proximal end of the body to an exterior axial surface of a closed distal end of the body, and (2) with a proximal section which extends from the proximal end of the body toward the closed distal end of the body, and to a distal end of the proximal section. The proximal section of the body is formed with an axial entry passage extending through the proximal section from the proximal end of the body toward a the closed distal end of the body, and to a distal end of the axial entry passage, which is formed with a prescribed diameter at the proximal end of the body.

The body is formed with an axial intermediate passage having a proximal end in communication with the distal end of the axial entry passage, which extends toward the closed distal end of the body, and to a distal end of the axial intermediate passage, with the axial intermediate passage being formed with a uniform passage diameter which is less than the prescribed diameter. The body is formed about the axis thereof with a passage section, having a uniform exterior diameter, which extends from a proximal end thereof toward the closed distal end of the body, and to a distal end of the passage section. The passage section of the body fully surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage.

At least one axially-elongated slot is formed radially through the slot section of the body in unobstructed communication with the axial slot delivery passage and an external surface of the body, and extends from the proximal end of the slot section toward the distal end of the slot section, and to a distal end of the at least one axially-elongated slot. The slot delivery passage is formed with the uniform passage diameter interrupted only by the presence of the at least one axially-elongated slot, which is formed with an extended side wall extending axially from a proximal end to the distal end of the at least one elongated slot. The extended side wall is located at one side of the at least one elongated slot, and extends from an inboard juncture of the extended side wall with the slot delivery passage to an outboard juncture of the extended side wall with the external surface of the body. A flat surface is formed in the body adjacent the at least one elongated slot, and has a first end spaced from the extended side wall. The flat surface extends from the first end thereof angularly away from the extended side wall to a second end of the flat surface at a juncture with the external surface of the body, and extends axially along at least a portion of the at least one elongated slot.

As further contemplated by this invention, an applicator includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at one side of the slot, and extends from an inboard juncture of the extended side wall with the slot delivery passage to an outboard juncture of the extended side wall with the common external surface of the stem. A flat surface is formed in the stem adjacent the slot, has a first end spaced from the extended side wall, and extends from the first end thereof angularly away from the extended side wall to a second end of the flat surface at a juncture with the common external surface of the stem.

This invention further contemplates an applicator which includes a body having a stem formed with a common external surface. A slot delivery passage, having a surrounding wall, is formed axially through at least a portion of the stem, and a slot is formed radially through a portion of the stem, from a mouth in the wall at a juncture of the wall of the slot delivery passage and the slot, to the common external surface.

The slot is formed with a single extended side wall which extends axially, along one side of the slot, from a proximal end to the distal end of the slot. The single extended side wall is located at one side of the slot, and extends generally radially outward from an inboard juncture of the extended side wall with the mouth of the slot delivery passage to an outboard juncture of the extended side wall with the common external surface of the stem. A flat surface is formed in the stem adjacent the slot, and has a first end at a juncture with the mouth, which juncture is spaced from the inboard juncture of the extended side wall with the mouth. The flat surface extends from the first end thereof angularly away from a the mouth of the and from the extended side wall, the flat surface extending to the its juncture with the common external surface.

This invention also contemplates an applicator for dispensing a medicinal substance therethrough, including a body formed about an axis with the body extending from a proximal end of the body to a distal end of the body. A stem forms an axial portion of the body, and is formed with a common external surface. A slot delivery passage is formed axially through at least a portion of the stem, with a slot formed through a portion of the stem from the slot delivery passage to the common external surface to facilitate the flow of the medicinal substance from within the slot delivery passage, through the slot, and to an environment adjacent the common external surface. The slot is formed with an extended side wall which extends axially from a proximal end to the distal end of the slot, with the extended side wall located at one side of the slot, and extending from an inboard juncture of the extended side wall with the slot delivery passage to an outboard juncture of the extended side wall with the common external surface of the stem. A flat surface is formed in the stem adjacent the slot, and has a first end spaced from the extended side wall. The flat surface extends from the first end thereof angularly away from the extended side wall to a second end of the flat surface at a juncture with the common external surface of the stem, with the flat surface and the extended side wall extending axially along at least a portion of the slot.

This invention also contemplates a method of delivering cream through a cream passage, which comprises the steps of feeding cream through an entry of a cream passage, through the cream passage, and to an exit of the cream passage; precluding any lateral movement in a first direction of a first portion of the cream as the first portion of the cream is fed from the entry to the exit of the cream passage; and feeding a second portion of the cream laterally of the first portion of the cream in a second direction opposite the first direction as the second portion of the cream is fed to the exit of the cream passage.

This invention contemplates a method of delivering cream through a cream passage further comprising the step of forming the exit with a first open portion and a second open portion which is contiguous with the first open portion.

This invention also contemplates a method of delivering cream through a cream passage wherein the entry of the cream passage is formed of a prescribed size and the exit of the cream passage is larger than the prescribed size.

This invention further contemplates a method of delivering cream through a cream passage further comprising the steps of establishing a prescribed distance between the entry and the first portion of the exit, and precluding the feeding, for a distance less than the prescribed distance, of the second portion of the cream laterally through the cream passage This invention contemplates a method of delivering cream through a cream passage further comprising the steps of positioning a first cream-receiving surface at a first portion of the exit, and positioning a second cream-receiving surface at a second portion of the exit.

This invention also contemplates a method of delivering a cream through a cream passage further comprising the step of directing the second portion of the cream angularly in a second direction opposite the first direction as the cream is moved laterally from the first portion of the cream.

The invention also contemplates a method of delivering a cream through a cream passage further comprising the steps of feeding the first portion of the cream directly onto the first cream-receptive surface, and spreading the second portion of the cream onto the second cream-receptive surface.

BRIEF DESCRIPTION OF THE DRAWINGS

In the accompanying drawings:

FIG. 7 is a front view of a first current applicator, as described, illustrated, and claimed in this application, showing a splined-edge flange near a proximal end of the applicator, and further showing one of two axially-elongated, diametrically-opposed slots, with each slot formed with a single extended side wall on one side of the slot, the first current applicator further formed with a flat, angular, or multi-configured surface, (hereinafter the "flat surface"), which extends angularly laterally away from the single extended side wall, and a transaxis plane parallel to the single extended side wall, and toward a common external surface of the first current applicator, the flat surface extending axially from a proximal end to a distal end of the slot to facilitate the application of a medicinal cream through the full axial length of the slot, over and outwardly from the flat surface, and onto tissue of body openings of a patient, in accordance with certain principles of the invention;

FIG. 8 is a side view showing additional features of the first current applicator of FIG. 7, in accordance with certain principles of the invention;

DETAILED DESCRIPTION OF THE INVENTION

Figure 1:
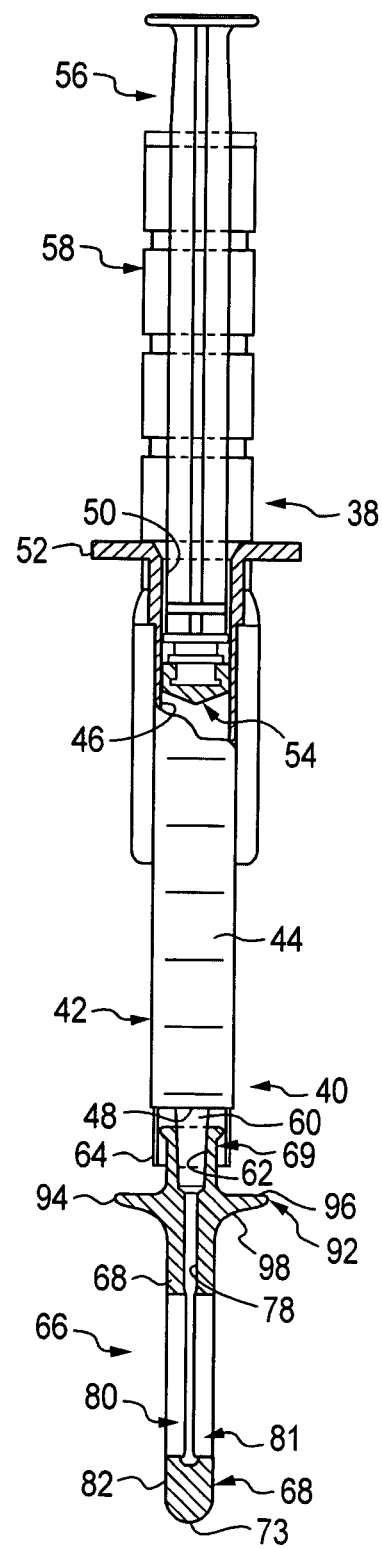
FIG. 1 is a partially-sectioned top view showing a focused dosimetry device, which is supporting a syringe, where a cartridge of the syringe is nested in a carrier of the device having spaced grooves for receiving a flange of the syringe, and further showing the syringe in assembly with a first prior applicator having slots of the type described, and illustrated, in U.S. Pat. No. 7,125,394.

As noted above, various medical conditions frequently exist within affected tissue areas of openings of the human body, such as, for example, natural openings of the anatomy of the human body, including, but not limited to, the vaginal opening and the anal opening, and unnatural openings such as, for example, but not limited to, surgically-formed openings, and/or openings resulting from injury. Each of the above-noted natural and unnatural openings is hereinafter referred to as "a body opening."

Also, as noted above, the terms "applicator," "tip," and "dispenser," have been used interchangeably, in the past, to refer to a cream-dispensing component, of the type which is the subject of the invention as described, claimed, and illustrated herein. For purposes of consistency in the description below, the term "applicator," will be used throughout, it being understood that such use also refers to the terms "tip" and "dispenser."

Further, two prior applicators are shown herein in FIGS. 1 through 6, 6a and 6b, each of which has a cream-passage slot, the width of which is defined by spaced, parallel, side walls. Such parallel side walls are described and illustrated in U.S. Pat. No. 7,141,036, which issued on Nov. 28, 2006.

Containers, for storing a medicinal substance, to which the applicators are attachable, are described below, and are used to facilitate the dispensing of the medicinal substance, such as, for example, a medicinal cream, compound, or the like, (hereinafter referred to as "the cream"), onto affected tissue of body openings of a patient, when the applicators are located adjacent the tissue.

The consistency of the cream is such that the cream does not flow easily within or out of the containers without a force being applied to the stored mass thereof to move the cream from the containers into the respective applicator.

One example of a supply container for storing the medicinal substance is a rapid-delivery system, such as, for example, a piston-operable syringe, which can be used in conjunction with, or used without, the above-noted focused dosimetry device, as described below in more detail. A volume of the cream is deposited into a barrel of the syringe, and the applicator is attached to a distal or output end of the syringe. The syringe is operated in a conventional manner to force the cream from within the barrel, into the applicator, through slots of the applicator, and onto the affected tissue of body openings of the patient, which are adjacent outboard portions of the slots.

The volume of the cream deposited initially into the barrel of the cartridge can represent multiple doses of the cream, wherein several single doses can be administered successively through the applicator over a period of time. Alternatively, the volume of the cream deposited initially into the barrel of the cartridge can also represent sufficient cream for administering, through the applicator, a single dose only, rather than multiple doses.

Another example of a supply container for storing the cream is a squeeze tube, such as, for example, the type typically used to store toothpaste, and facilitate dispensing the toothpaste by squeezing the tube. The tube includes an enclosure formed by a flexible wall with a single outlet, which is sealed by a removable cap during periods when it is desired to retain the cream within the enclosure. When it is desired to urge the cream from within the enclosure of the tube, the cap is removed from the single outlet of the tube and the applicator is substituted therefor. By virtue of the flexible wall of the tube, the tube can be squeezed, pinched, or the like, to urge the cream from within the enclosure, through the single outlet, into the applicator, and through slots thereof to administer the cream onto the tissue within the body opening of the patient.

Various embodiments of prior applicators, and current applicators, as described below, are particularly useful for applying and focusing each administered dose of the cream to affected tissue areas of vaginal and/or anal openings of the human anatomy, but can be used for applying and focusing the cream to tissue within any natural and/or non-natural body openings of the human body.

As described below, the above-noted "prior" applicators refer to applicators having features, which have been previously disclosed, such as, for example, the applicator disclosed in the above-mentioned U.S. Pat. No. 7,141,036. As also described below, the "current" applicators refer to applicators having features currently disclosed, claimed and illustrated in this application.

The below-described embodiments of the applicator include a first axial, or proximal, end, at which the cream enters the applicator, and a second axial, or distal, end spaced axially distally from the first axial end. The end of any structural portion, such as, for example, an axially extending slot, of each of the various embodiments of the applicator, which is closest to the proximal end of the applicator, will be referred to as the proximal end of such structural portion, and the other end of such structural portion or applicator, which is opposite the proximal end, will be referred to as the distal end. For example, an axially extended slot formed radially through a body of the applicator will extend between a proximal end and a distal end of the slot.

Figure 6:
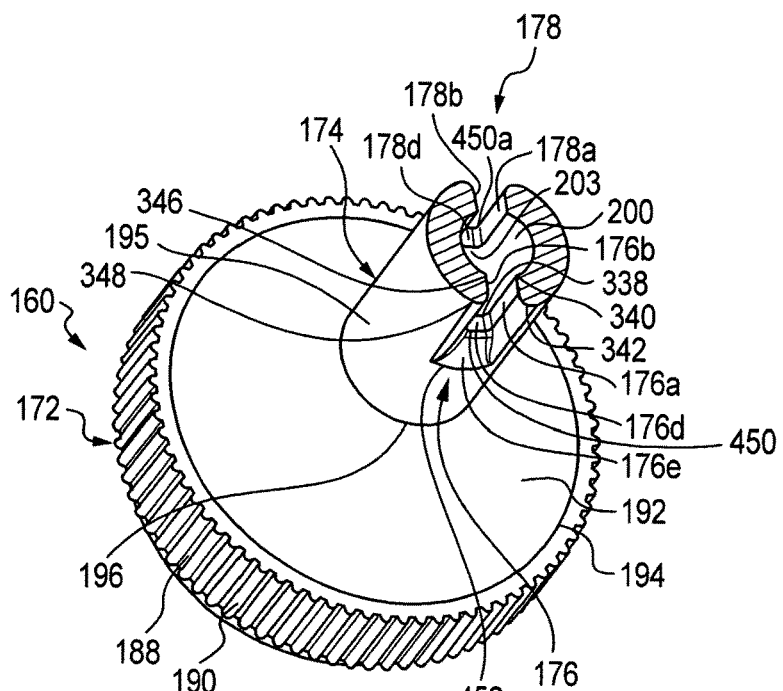
FIG. 6 is a partially-sectioned, perspective view showing a portion of the second prior applicator of FIG. 5 with the slot section of the body thereof being sectioned to show interior structure of the body and to show the two spaced, parallel, interfacing, first and second extended side walls of each the two slots.
Figure 6A:
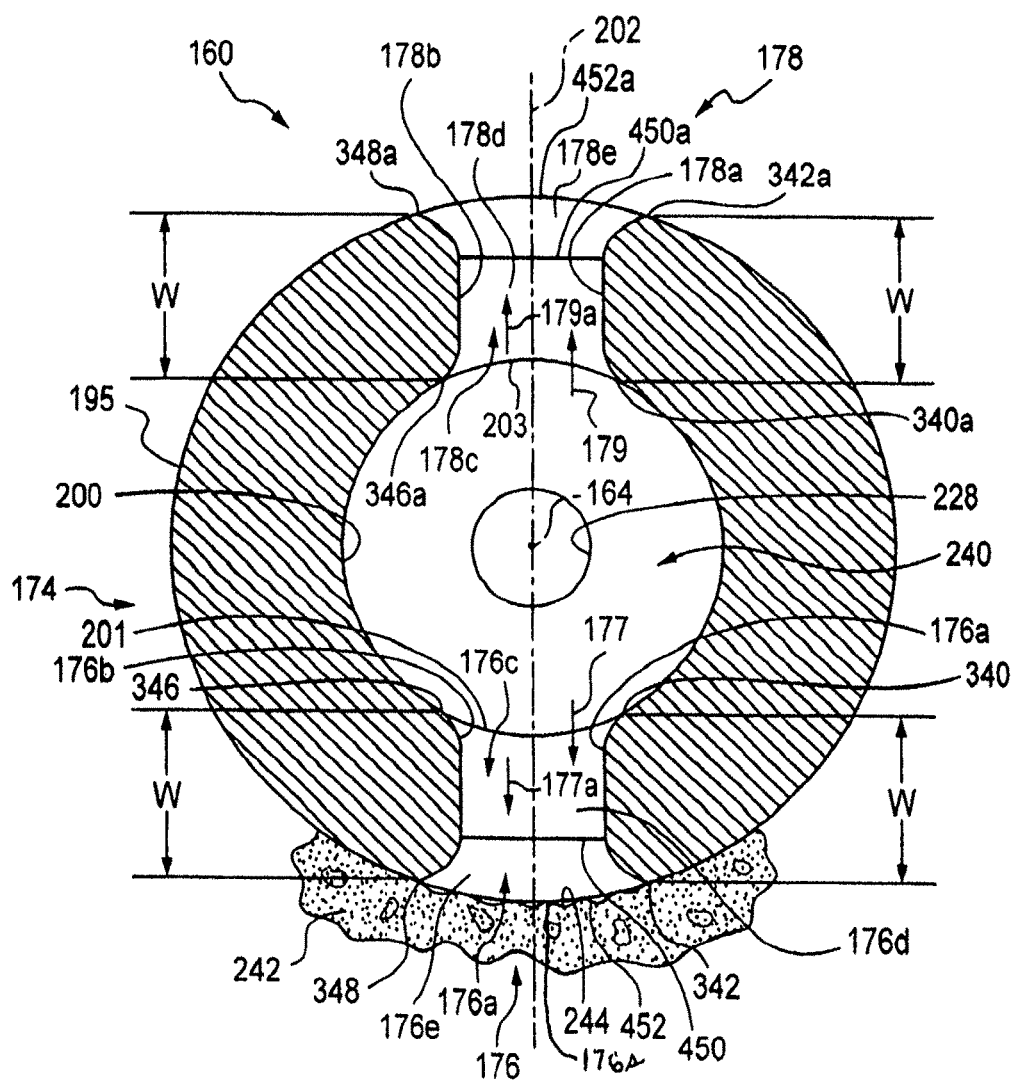
FIG. 6a is an enlarged sectional view, taken along line 6a-6a of FIG. 5, showing the spaced relationship of the two parallel, interfacing first and second extended side walls of each of the two slots of the body of the second prior applicator of FIG. 5, with the flange extracted from the sectional view for clarity purposes.

As shown in FIGS. 6*a*, a cream 280 is being applied onto selected surfaces of a tissue 242 within a body opening 244 of a patient.

Referring to FIG. 1, a first technique for applying the cream 280 (FIGS. 6*a* and 12) to the surfaces of the tissue 242 could include the use of a focused dosimetry device 38, described, claimed, and illustrated in U.S. Pat. No. 8,845,596, which issued on Sep. 30, 2014. The device 38 is typically used in multiple dose applications, but can be used for single dose applications, as well. The device 38 can support, and is used with, a syringe 40, which includes a cartridge 42 having a barrel 44. The syringe 40 serves as a rapid-delivery, cream-supply container for storing the cream 280 therein, or storing any other substance having a cream-like consistency.

In the syringe 40, the barrel 44 is formed with a hollow interior barrel passage 46, having a distal opening 48 at a distal end thereof and a proximal opening 50 at a proximal end thereof. A flange 52 is formed radially outward on the barrel 44 at the proximal end thereof. The syringe 40 further includes a plunger 54, which is located within the barrel passage 46, and a stem 56, which is insertable into the proximal opening 50. This structural arrangement facilitates movement of the plunger 54 within the barrel passage 46 toward the distal opening 48 thereof, to dispense the cream 280 externally from within the barrel passage, at the distal end of the cartridge 42.

The device 38 includes a carrier 58, which supports the cartridge 42 and the stem 56 during use of the device, and, in conjunction with the flange 52 of the barrel 44, facilitates the dispensing of successive single-dose applications, or a single dose only, of the cream 280 from the barrel.

Figure 3:
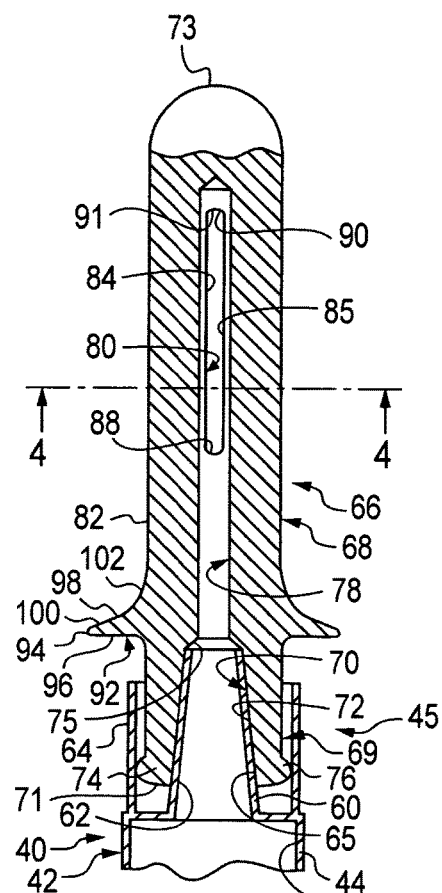
FIG. 3 is an enlarged partial sectional view showing a proximal end of the first prior applicator in assembly with a distal end of the syringe of FIG. 1.

As shown in FIGS. 1 and 3, the syringe 40 is formed with a small-diameter sleeve 60 at the distal end thereof, which is an integral part of the cartridge 42, is in axial alignment with the barrel 44 at the distal end thereof, and forms a sleeve passage 62 in communication with the barrel passage 46. The exterior of the small-diameter sleeve 60 is tapered in the form of a frustum, with the smaller diameter of the frustum located at the distal end of the sleeve, and the axis of the frustum being coincidental with the axis of the barrel 44.

A large-diameter sleeve 64 is also an integral part of the cartridge 42, at the distal end thereof, and is in axial alignment with the barrel 44, and in coaxial alignment with, and about, the small-diameter sleeve 60. An internal cylindrical wall of (1) the large-diameter sleeve 64 can be unthreaded, such as shown, for example, in FIG. 3, or (2) a similar large-diameter sleeve 64*a* can be threaded, such as shown, for example, in FIGS. 17 through 22. The proximal end of the large-diameter sleeve 64 is closed (FIG. 3) and not in communication with the barrel passage 46, and serves as a stop surface 49 for limiting distal movement of the plunger 54 within the barrel passage.

The structure of the small-diameter sleeve 60 and the large diameter sleeve 64 combine to form a cartridge coupler portion 67 of a coupling assembly 45, which will described, in more detail below.

A more detailed description of the structure and the operation of the device 38, in conjunction with the syringe 40, is described in the above-noted U.S. Pat. No. 8,845,596 which is incorporated herein by reference thereto.

Figure 2:
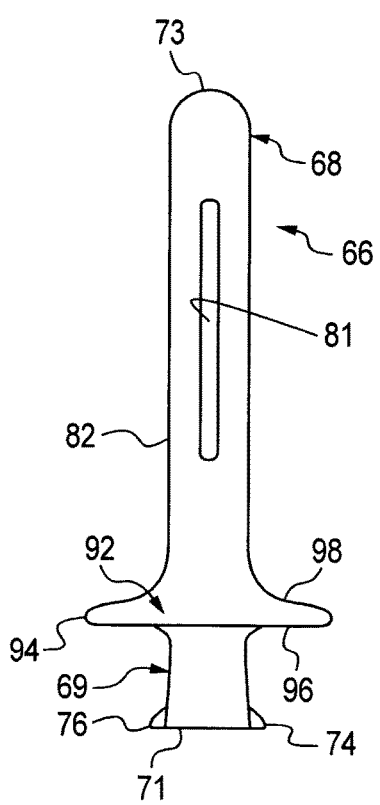
FIG. 2 is a side view showing structure of the first prior applicator of FIG. 1, including two, spaced, parallel, interfacing, extended side walls, which define a cream-dispensing slot of the applicator.
Figure 4:
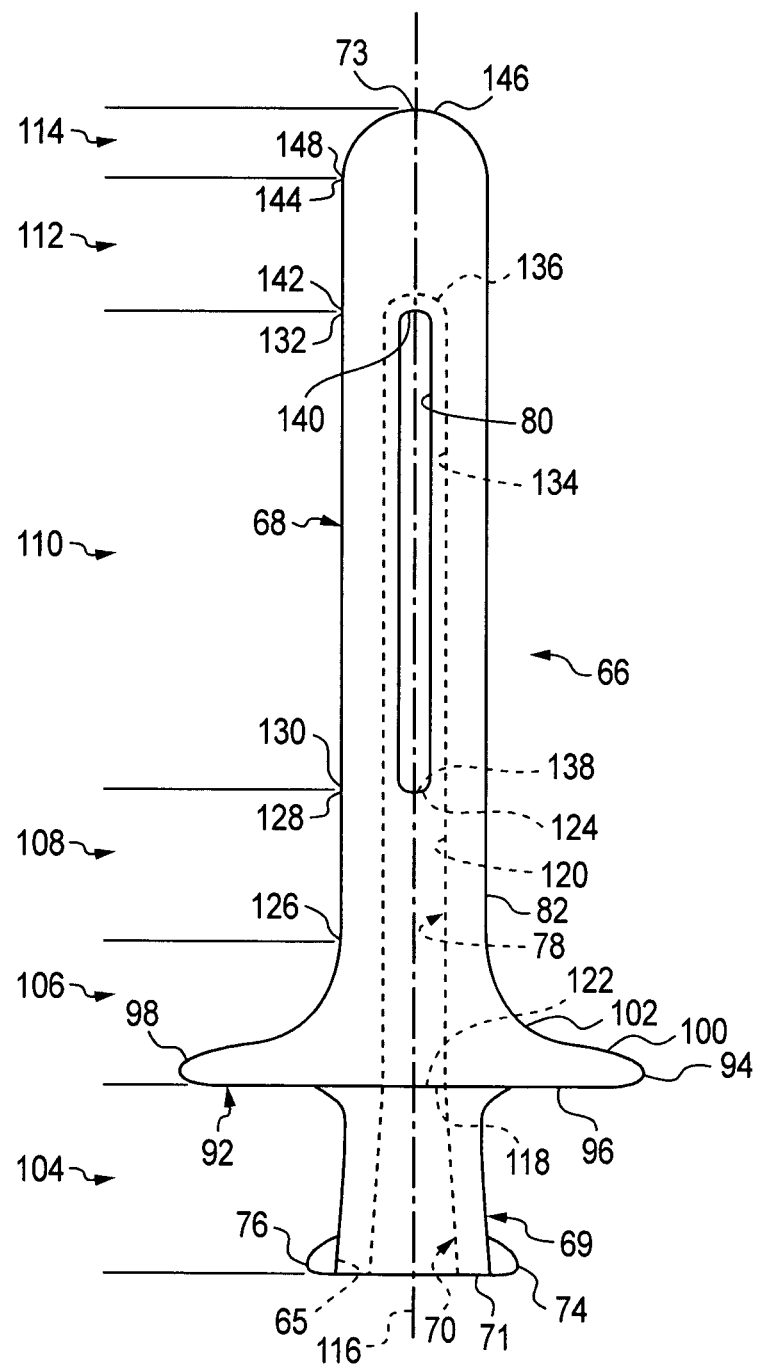
FIG. 4 is a side view showing the first prior applicator of FIGS. 1 and 2 formed with integrally-joined sections.

Referring to FIGS. 1 through 4, a first prior applicator 66 has a body 68, which, as shown in FIGS. 2, 3, and 4, is formed with an applicator coupler portion 69 of the coupling assembly 45, and having an axial entry passage 70 therein. The applicator portion 69 of the first prior applicator 66 is assembled with the cartridge coupler portion 67 of the cartridge 42 at the distal end of the barrel 44, in the form of the coupling assembly 45 such as the coupling assembly associated with U.S. Registered Trademark LUER-LOK, which is owned by Becton, Dickinson and Company, having an office in Franklin Lakes, N.J.

In particular, as shown in FIG. 3, the axial entry passage 70 of the first prior applicator 66 is formed with a tapered wall 72 which tapers axially inward from a proximal end of the passage to a distal end thereof, and which mates with the exterior taper of the sleeve 60 of the cartridge 42 to facilitate one aspect of the attachment of the first prior applicator with the cartridge. The axial entry passage 70, which is formed with a prescribed diameter at a proximal end 71 of the body 68, extends from the proximal end of the body 68 toward a distal end 73 of the body and to a distal end 75 of the axial entry passage. The body 68 of the first prior applicator 66 is formed within a first ear 74 and a second ear 76, which extend outward in radially opposite directions from the proximal end of the first prior applicator.

As the first prior applicator 66 is being assembled with the cartridge 42, the outboard ends of the ears 74 and 76 are inserted within the large-diameter sleeve 64 with axial and/or rotational forces applied to the first prior applicator to frictionally assemble the applicator with the syringe 40, by the coupling assembly 45. Rotation of the first prior applicator 66 frictionally enhances the assembly of the tapered small-diameter sleeve 60 with the tapered proximal opening 72 of the axial entry passage 70. The assembly of the syringe 40 with the applicator 66 is referred to as a cream delivery assembly 67.

It is noted that facilities, other than as described above, can be used to attach the first prior applicator 66 to the cartridge. Such attachment facilities could be threaded, unthreaded, tapered, press fit, or the like.

As further shown in FIG. 3, the first prior applicator 66 is also formed with an inner axial delivery passage 78, which extends axially of the body 68, with a uniform diameter, between an open proximal end 75 and a closed distal end 90 of the axial delivery passage. The axial entry passage 70 is in communication with the axial delivery passage 78, with the distal end of the axial entry passage and the proximal end of the axial delivery passage being located at the transaxial juncture of the passages. In the first prior applicator 66, the uniform diameter of the axial delivery passage 78 is less than the prescribed diameter of the axial entry passage 70 at the proximal, or entry, end 71 of the passage 70.

The axial entry passage 70 could be formed in a configuration other than the tapered wall. The uniform diameter of the axial delivery passage 78 is less than the prescribed diameter of the axial entry passage 70 at the proximal, or entry, end 71 of the axial entry passage.

A pair of diametrically-opposed axially extending, elongated slots 80 (FIG. 3) and 81 (FIG. 2) are formed in the body 68. Each of the slots 80 and 81 are in communication with, and extend radially through the body 68 from, the axial delivery passage 78 and exit at a common external surface 82 on opposite sides of the body, adjacent exterior portions of the slots. As shown in FIG. 3, the slot 80 is formed with two spaced, axially-extending, interfacing, parallel side walls 84 and 85 (FIG. 3), which extend from a proximal end 88 of the slot to a distal end 91 thereof, and define the width of the slot. For brevity, each of the side walls 84 and 85 are referred to hereinafter as "an extended side wall."

In similar fashion, the slot 81 (FIG. 2) is formed with spaced, axially-extending interfacing, parallel side walls (i.e., extended side walls), which extend from a proximal end of the slot 81 to a distal end thereof, and define the width of the slot. The axial entry passage 70, the axial delivery passage 78, and the slots 80 and 81 are all in communication with each other to facilitate the smooth flow of the cream 280 from the barrel 44 and through the first prior applicator 66 to locations externally of the first applicator. It is noted that, while the above-described first prior applicator 66 includes the pair of slots 80 and 81, the first prior applicator could be formed with a single slot, or more than two slots.

Referring further to FIG. 3, the first prior applicator 66 is formed with a tactile-indicating flange 92 near the proximal end 71 thereof. The applicator body 68 is formed with the common external surface 82 of a uniform external diameter, and extends from the flange 92 nearly to the distal end 73 of the body, and is interrupted only by the openings of the slots 80 and 81 formed in the common external surface.

The flange 92 extends radially outward from the common external surface 82 of the body 68 to an outer edge surface 94 of the flange. The flange 92 is formed with a proximal surface 96 facing in a direction toward the proximal end 71 of the body 68 and a distal surface 98 facing in a direction toward the distal end 73 of the body. The distal surface 98 of the flange 92 is formed by a straight portion 100 which extends from the outer edge surface 94 of the flange, radially inward toward the axis of the body 68 and toward the distal end 73 of the body, to an inboard edge of the straight portion spaced radially outward from the external surface of the body. The distal surface 98 of the flange 92 is formed with a concave portion 102 which extends from the inboard edge of the straight portion 100 toward the distal end 73, and to the common external surface 82, of the body 68. The flange 92, with the concave portion 102 and the angled flat portion 100, provides a user-friendly tactile indication to the patient that the first prior applicator 66 has been inserted into body openings at the appropriate distance for placement of the slots 80 adjacent the tissue areas to be treated with the cream 280.

Referring to FIG. 4, and in an alternative manner of describing the first prior applicator 66, which is also shown in FIGS. 1, 2 and 3, the first prior applicator includes the unitary body 68, formed by six integrally-joined sections, identified as a proximal section 104, a flange section 106, a passage section 108, a slot section 110, a solid section 112, and a dome section 114.

As noted above, the first prior applicator 66 is designed to facilitate the dispensing of the cream 280 therethrough, where the cream has a consistency of the type which does not flow without a force being applied thereto.

The body 68 of the first prior applicator 66 is formed about an axis 116, which extends from the proximal end 71 of the body to the closed distal end 73 of the body.

The proximal section 104 of the body 68 is formed with the axial entry passage 70, which extends from the proximal end 71 of the body toward the closed distal end 73 of the body, and to a distal end 118 of the axial entry passage. The axial entry passage 70 is formed with a prescribed diameter, at least at the proximal end 71 of the body 68.

The body 68 is also formed with an axial intermediate passage 120 having a proximal end 122, which is coincidental with the distal end 118 of the axial entry passage 70. The axial intermediate passage 120 is formed with a uniform passage diameter, which is less than the prescribed diameter, and extends toward the closed distal end 73 of the body 68, and to a distal end 124 of the axial intermediate passage.

The body 68 is formed about the axis 116 thereof with the passage section 108, which has a uniform exterior diameter. The passage section 108 extends from a proximal end 126 thereof toward the closed distal end 73 of the body 68, and to a distal end 128 of the passage section, and fully surrounds at least a portion of the axial intermediate passage 120 to the proximal end 124 thereof.

The body 68 is formed about the axis 116 thereof within the slot section 110, and is formed with the uniform exterior diameter. The slot section 110 extends from a proximal end 130 thereof toward the closed distal end 73 of the body 68, and to a distal end 132 of the slot section, with the proximal end 130 of the slot section formed integrally with the distal end 128 of the passage section 108.

A slot delivery passage 134 is formed axially through the slot section 110 of the body 68 from the proximal end 130 of the slot section toward the closed distal end 73 of the body, and to a closed distal end 136 of the slot delivery passage, with a proximal end 138 of the slot delivery passage being in communication with the distal end 124 of the axial intermediate passage 120.

The axially-elongated slot 80 (hereinafter "the at least one axially-elongated slot 80") is formed radially through the slot section 110 of the body 68 in unobstructed radial communication with the slot delivery passage 134 and an exterior of the body, and extends from the proximal end 130 of the slot section toward the distal end 132 thereof, and to a distal end 140 of the at least one axially-elongated slot 80. The slot delivery passage 134 is formed with the uniform passage diameter, interrupted only by the presence of the at least one axially-elongated slot 80.

The body 68 is formed with the solid section 112, having the uniform exterior diameter, which extends from a closed proximal end 142 of the solid section toward the closed distal end 73 of the body, and to a closed distal end 144 of the solid section. The closed proximal end 142 of the solid section 112 is formed integrally with the distal end 132 of the slot section 110.

The body 68 is formed with the dome section 114 in the form of a solid dome 146, which extends from a closed proximal end 148 of the dome section to the closed distal end 73 of the body, with the closed proximal end being coincidental with the exterior axial surface of the dome. The closed proximal end 148 of the dome section 114 is formed integrally with the closed distal end 144 of the solid section 112. The solid section 112 and the dome section 114 are exclusive of any opening therethrough.

It is noted that the axial intermediate passage 120 of the passage section 108, and the slot delivery passage 134 of the slot section 110, are axially aligned and combine to form the axial delivery passage 78 as illustrated in FIG. 3. Further, as described above, and with reference to FIG. 4, the axially aligned axial intermediate passage 120 and the slot delivery passage 134 are formed with the uniform passage diameter.

As further shown in FIG. 4, the flange 92 is located in the flange section 106, between the proximal section 104 and the passage section 108. The flange 92 is integrally joined with adjacent portions of the body 68, at opposite axial ends of the flange, and fully radially surrounds a portion of the axial intermediate passage 120. Thus, except for the presence of the at least one axially-elongated slot 80, successive portions of the body 68, which are located in the three sections identified as the flange section 106, the passage section 108 and the slot section 110, surround the axial delivery passage 78 (FIG. 3), which, as noted above, is formed by the axial intermediate passage 120 and the slot delivery passage 134 illustrated in FIG. 4.

The exterior structure of the flange 92, as illustrated in FIG. 4, is described above with respect to FIG. 3, and is not further described herein.

With the structure of the body 68 as described above, there is full communication from an exterior of the body, at the proximal end 71 thereof, through the axial entry passage 70, the axial intermediate passage 120, the slot delivery passage 134, the at least one axially-elongated slot 80, and an exterior of the body adjacent the at least one axially-elongated slot.

Referring to FIGS. 5, 6, 6a, and 6b, a second prior applicator 160 has an integrally-formed, unitary body 162, which extends axially along an axis, or centerline, 164 between a proximal end 166 and a closed distal end 168 of the body. The body 162 is formed integrally with (1) a proximal coupler 170 which extends axially from the proximal end 166 of the body, (2) an axially-elongated circular flange 172, (3) an axially-elongated stem 174 formed transaxially with two axially-elongated diametrically-spaced slots 176 and 178 (FIG. 6), (4) an axially-elongated solid spacer 180, and (5) an axially-elongated dome 182 which extends axially to the distal end 168 of the body.

A distal end of the proximal coupler 170 is joined integrally, at a juncture 184 (FIG. 6b), with a proximal side of the flange 172, and is formed with a cylindrical exterior surface 186 having a prescribed external diameter. The flange 172 is formed with a cylindrical exterior surface 188 having an external diameter which is greater than the prescribed external diameter. To facilitate manually-controlled rotation of the second prior applicator 160, the perimeter of the exterior surface 188 of the flange 172 is formed with parallel, axially-aligned, spaced serrations, or splines, 190, which enhance manual gripping of the exterior surface of the flange.

The flange 172 is further formed with an external, concave, distal surface 192, which extends integrally between a distal edge 194 of the cylindrical exterior surface 188 and a juncture 196 of a distal end of the concave distal surface and a proximal end of the stem 174. The stem 174 and the solid spacer 180 are formed with a common external surface 195, having an external diameter, which is less than the prescribed external diameter. The stem 174 and the solid spacer 180 are integrally joined at a juncture 198 (FIG. 6b) of a distal end of the stem and a proximal end of the solid spacer. A distal end of the solid spacer 180 is integrally joined with a proximal end of the dome 182 at a juncture 199 (FIG. 6b) thereof. Also, the solid spacer 180 and the dome 182 are solid, and do not have any passages, slots, or the like formed therethrough.

Figure 6B:
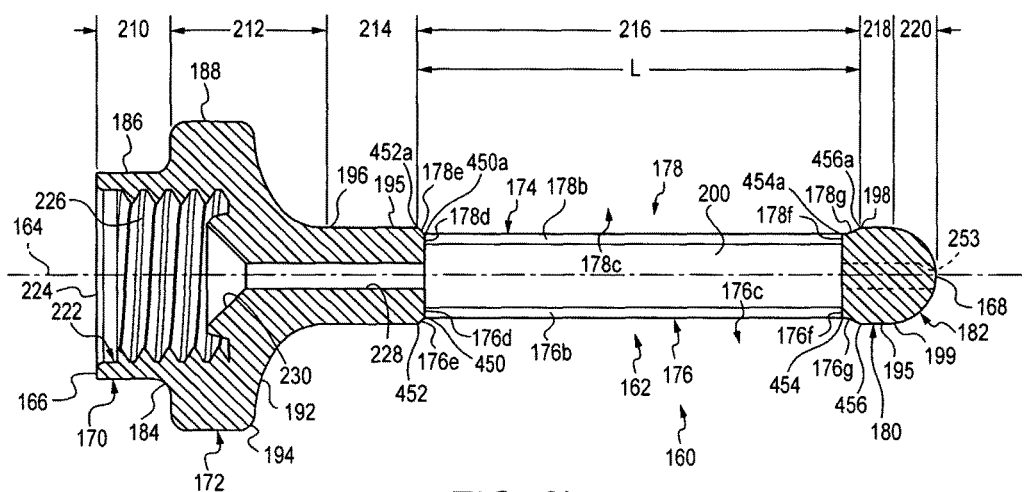
FIG. 6b is a sectional view, taken along line 6b-6b of FIG. 5, showing internal structure of the second prior applicator of FIG. 5 with integrally-joined sections thereof, and formed with axially-aligned, internal, communicating passages of different diameters.

Referring to FIGS. 6a and 6b, the stem 174 is formed axially with a slot delivery passage 200, having a prescribed internal diameter, which communicates with the axially-elongated slots 176 and 178. The slot 176 includes a first extended side wall 176a and a second extended side wall 176b, which are parallel to each other, and which define a space 176c, or confined passage, therebetween, for guiding the cream 280 (FIG. 12) therethrough in a direct flow path indicated by arrows 177 and 177a.

Note that due to the confined space between the side walls 176a and 176b, and due to the presence of the side walls to the cream 280 passing through the slot 176, the side walls serve as a barrier to any movement of the cream laterally of the flow path indicated by the arrows 177 and 177a, whereby the cream flows directly through the slot from an entry 201 of the slot to an exit 176s thereof.

As shown in FIG. 6a, a transaxis, or centerline, 202 extends radially through, and from, the axis 164 and defines a transaxis plane coincidental with the transaxis. The extended side walls 176a and 176b are generally parallel to, and spaced from, each other, and to the transaxis plane of the transaxis 202.

A proximal wall 176d, or floor, is formed at a proximal end portion of the slot 176, and extends radially between (1) the entry 201, which is coincidental with a wall of the slot delivery passage 200, and (2) a distal straight-line juncture 450 of the proximal wall. A proximal transition surface 176e or ramp located at a slot exit 176s, is defined by the juncture 450 and a curved juncture 452. Further, the proximal wall 176d is integrally joined at opposite sides with, and extends between, proximal ends of the spaced, first and second extended side walls 176a and 176b, respectively. The proximal transition surface 176e is formed in the common external surface 195, and slopes outward, in a proximal direction, from the distal juncture 450 to the proximal juncture 452 of the proximal transition surface with the common external surface.

It is noted that the entry 201 of the slot 176 facilitates movement of the cream 280 into the slot 176, while the exit 176s of the slot 176 is formed at the ramp 176e to facilitate dispensing of the cream 280 from the slot. The well-defined travel path of the cream 280, formed by the spaced, parallel side walls 176a and 176b, facilitate the cream travelling directly from the entry 201 of the slot 176 to the exit 176s, and impinging directly onto the prepositioned surface of the tissue 242, as shown in FIG. 6a.

Further, at the distal end of the slot 176 (FIG. 6b), the slot includes a distal end wall, or floor, 176f between the spaced, first and second extended side walls 176a and 176b, respectively, at the distal ends thereof. A distal transition surface 176g is formed in the common external surface 195 in a manner similar to the forming of the proximal transition surface 176e, except that the distal transition surface slopes radially outward, in a distal direction, from a proximal juncture 454 thereof with the distal wall 176f to a distal juncture 456 thereof with the common external surface.

Figure 5:
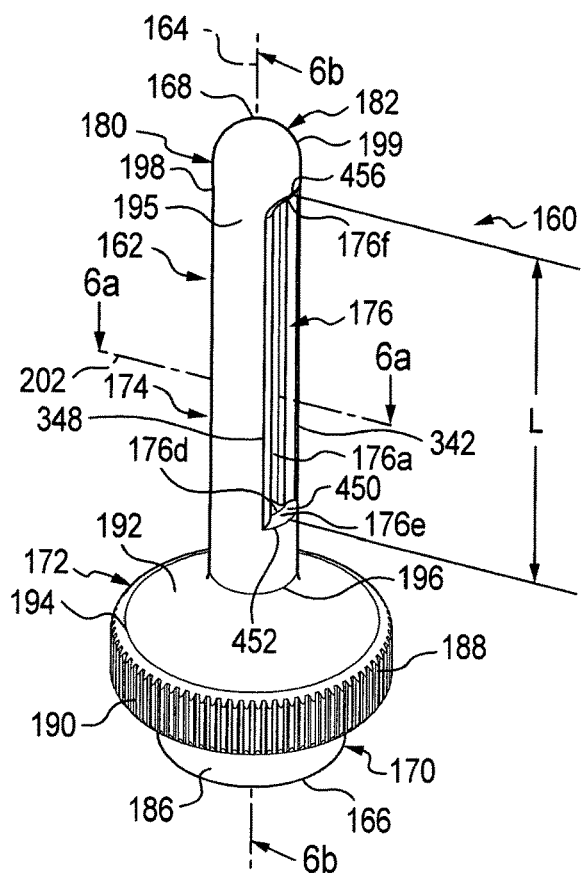
FIG. 5 is a perspective view showing a second prior applicator formed additionally with an axially-elongated, circular flange having a serrated or splined edge, and a generally cylindrical body, and further showing one of the two interfacing dispensing slots, of the type described, and illustrated, in the above-noted U.S. Pat. No. 7,125,394, formed in a slot section, or stem, of the body.

As shown in FIGS. 5 and 6b, the slot 176 extends, by a distance "L," axially between the proximal juncture 452 and the distal juncture 456. It is noted that the distal juncture 456 of the distal transition surface 176g is coincidental with the juncture 198 of the stem 174 and the solid spacer 180.

As shown in FIG. 6a, the first extended side wall 176a of the slot 176 is formed dimensionally with a width "W," which extends in a first direction from an integral junction 340 of the side wall with the slot delivery passage 200 to an integral junction 342 of the side wall with the common external surface 195. Also, the second extended side wall 176b of the slot 176 is formed dimensionally with the width "W," which extends in a second direction from an integral junction 346 of the side wall with the slot delivery passage 200 to an integral junction 348 of the side wall with the common external surface 195.

In the second prior applicator 160, the direction, in which the first extended side wall 176a extends from the slot delivery passage 200, is generally parallel with the direction, in which the second extended side wall 176b extends from the slot delivery passage. With this structural arrangement, the first and second extended side walls 176a and 176b, respectively, are generally parallel and spaced apart to define, along the axial length "L" of the slot 176, the direct flow path of the cream 280 through the slot, as indicated by the arrow 177 to the exit 176s of the slot, and onto the prepositioned surface of the tissue 242.

Referring to FIG. 6a, the entry 201 defines a mouth of the slot 176, which extends between the integral juncture 340, representing a first side of the mouth, and the integral juncture 346, representing a second side of the mouth spaced from the first side of the mouth.

It is noted that a prescribed volume of the cream passage of the slot 176 of the second prior applicator 160 is defined by the space between the extended side walls 176a and 176b, and the slot length "L" of the slot. The prescribed volume of the slot 178, of the second prior applicator 160, is defined in the same manner, with respect to the extended side walls 178a and 178b and the slot length "L".

Referring to FIGS. 5, 6a, and 6b, the slot 178 is structured identically to the slot 176, as described above. The slot 178 includes a first extended side wall 178a and a second extended side wall 178b, which define a space 178c, or confined passage, therebetween, for guiding the cream 280 (FIG. 6a) through an entry 203 of the slot, in a direct flow path through the slot, as indicated by an arrow 179, to an exit 178s and onto the surface of the propositioned tissue 242.

As shown in FIG. 6a, the extended side walls 178a and 178b are parallel to, and spaced from, each other, and to the transaxis plane of the transaxis 202, or centerline.

A proximal wall, or floor, 178d is formed at a proximal end portion of the slot 178, and extends radially between (1) the entry 203 of the slot, and (2) a distal straight-line juncture 450a of the proximal wall and a proximal transition surface 178e. Further, the proximal wall 178d is integrally joined at opposite sides with, and extends between, proximal ends of the spaced, parallel, first and second extended side walls 178a and 178b, respectively. The proximal transition surface 178e is formed in the common external surface 195, and slopes outward, in a proximal direction, from the distal juncture 450a to a proximal juncture 452a of the proximal transition surface with the common external surface.

Further, at a distal end portion of the slot 178, as shown in FIG. 6b, the slot includes a distal end wall, or floor, 178f between the spaced, parallel, first and second extended side walls 178a and 178b, respectively. A distal transition surface 178g is formed in the common external surface 195 in a manner similar to the forming of the distal transition surface 178e, except that the distal transition surface slopes radially outward, in a distal direction, from a proximal juncture 454a thereof with the distal end wall 176f to a distal juncture 456a thereof with the common external surface.

As shown in FIG. 6b, the slot 178 extends, by the distance "L," axially between the proximal juncture 452a of the proximal transition surface 178e, and the distal juncture 456a of the distal transition surface 178g. It is noted that the distal juncture 456a of the distal transition surface 178g is coincidental with the juncture 198 of the stem 174 and the solid spacer 180.

As shown in FIG. 6a, the first extended side wall 178a of the slot 178 is formed dimensionally with the width "W," which extends from an integral junction 340a of the side wall with the slot delivery passage 200 to an integral junction 342a of the side wall with the common external surface 195. Also, the second extended side wall 178b of the slot 178 is formed dimensionally with the width "W," which extends from an integral junction 346a of the side wall with the slot delivery passage 200 to an integral junction 348a of the side wall with the common external surface 195. In the second prior applicator 160, the first direction, in which the first extended side wall 178a extends from the slot delivery passage 200, is generally parallel with the second direction, in which the second extended side wall 178b extends from the slot delivery passage.

In this manner, each of the slots 176 and 178 provide a confined radial path for the travel of the cream 280 directly from the slot delivery passage 200, in opposite directions. The cream 280 passes through the respective slots along the length "L" of the slots, and generally parallel to the transaxis plane which is coincidental with the transaxis 202, to the environment (i.e., the surfaces of the tissue 242) surrounding the common external surface 195 of the stem 174. transaxis plane Referring to FIG. 6b, the unitary body 162 of the second prior applicator 160 is formed in six integrally-joined sections, namely the proximal section 210, the flange section 212, the passage section 214, the slot section 216, the solid section 218, and the dome section 220.

The proximal coupler 170 is located in the proximal section 210, and the flange 172 is located in the flange section 212. A proximal portion of the stem 174 is located in the passage section 214, and the remainder of the stem is located in the slot section 216. The solid spacer 180 is located in the solid section 218, and the dome 182 is located in the dome section 220.

As noted above, the slot delivery passage 200, which is located in the slot section 216, is formed with a prescribed internal diameter. A proximal portion of an axial entry passage 222 is formed in the proximal coupler 170, and has a proximal entry opening 224 which is coincidental with the proximal end 166 of the body 162. A distal portion of the axial entry passage 222 is formed axially, and terminates, in the flange 172. Internal threads 226 are formed in the axial entry passage 222, which has an internal diameter greater than the prescribed internal diameter of the slot delivery passage 200.

An axial intermediate passage 228 is formed partially in the flange 172 and partially in the stem 174, and extends distally from a proximal end of the passage, located in the flange, to a distal end of the passage, located in the stem 174. The axial intermediate passage 228 is formed with an internal diameter, which is significantly less than the prescribed internal diameter of the slot delivery passage 200, and is considerably less than the internal diameter of the axial entry passage 222. An axial, funnel-shaped, transition passage 230 is axially interposed between the distal end of the axial entry passage 222 and the proximal end of the axial intermediate passage 228.

The axial entry passage 222, the axial transition passage 230, the axial intermediate passage 228, the slot delivery passage 200, and the slots 176 and 178 are all in communication, so that the cream 280 entering the proximal entry opening 224, under external force, will eventually exit, through outboard portions of the slots, to the environment externally of the body 162.

In the second prior applicator 160, the axial length of the slot delivery passage 200 (26 mm) is approximately two and one-half times the axial length of the axial intermediate passage 228 (10.65 mm). In addition, the diameter of the slot delivery passage 200 (3.18 mm) is approximately two and three-fifths times the diameter of the axial intermediate passage (1.22 mm). With the length and diameter of the slot delivery passage 200 as noted above, a sizable chamber 240 is formed by the slot delivery passage for the reception of significant amounts of the cream 280 within the chamber during use of the second prior applicator 160, for ultimate application of the cream 280 onto surfaces of the tissue 242 (FIG. 12) of a body opening 244 (FIG. 12) of the patient.

When the second prior applicator 160 is attached to, and used with, a rapid-delivery supply container, such as, for example, the piston-operable syringe 40 (FIG. 1), the cream 280 exits the syringe at a comparatively high-flow rapid-delivery rate. If the second prior applicator 160 had been formed with an axial intermediate passage having the same prescribed internal diameter as the slot delivery passage 200, the cream 280 would be fed directly into the slot delivery passage at the above-noted high-flow rate.

In this instance, the cream 280, travelling at the high-flow rate, would tend to exit proximal portions of the slots 176 and 178 before the chamber 240 can be substantially filled with the cream. This action would result, undesirably, in large amounts of the cream 280 being dispensed onto the surfaces of tissue 242 of the body opening 244 adjacent proximal portions of the slots 176 and 178, and smaller amounts deposited onto the surfaces of the tissue adjacent distal portions of the slots.

This disparity of application of the cream 280 onto the surfaces of adjacent tissue 242 is alleviated by forming the axial intermediate passage 228 with the above-noted relatively smaller diameter and relatively shorter length, which is considerably less than the diameter and length of the slot delivery passage 200.

Although limited amounts of the cream 280 exit through proximal portions of the slots 176 and 178 before the chamber 240 is filled, the above-noted parametrical relationships amongst the diameters and lengths of the axial intermediate passage 228 and the slot delivery passage 200 enhance the ability of the second prior applicator 160 to allow the chamber 240 to fill with the cream before significant amounts of the cream exit through the slots 176 and 178. This provides for a relatively even distribution of the cream 280 along the axial length "L" of the slots 176 and 178 after the chamber 240 is essentially filled with the cream.

In the second prior applicator 160, the solid spacer 180 and the dome 182 are solid as noted above. However, as shown in FIG. 6b, a distal passage 253 could be formed axially through the solid spacer 180 and the dome 182 from and through a distal end of the slot delivery passage 200 to and through the distal end 168.

As shown partially at the bottom of FIG. 6a, when the stem 174 of the second prior applicator 160 is inserted into the body opening 244, surfaces of the tissue 242 are located at the radially outboard side of the slot 176. A similar condition occurs at the radially outboard side of the slot 178. If the surfaces of the tissue 242 at the radially outboard sides of the slots 176 and/or 178 are dense, and/or the body opening 244 is small compared to the diameter of the stem 174, significant opposition to the outflow of the cream 280 onto the surfaces may result. This opposition results in an insufficient amount of the cream 280 being applied to surfaces of the tissue 242, which are adjacent the radially outboard sides of the slots 176 and 178.

As shown in FIG. 3, it is important to note that the slot 80 of the prior applicator 66 is well defined by the spaced, parallel, interfacing, extended side walls 84 and 85, which results, in the manner shown in FIG. 6a, in the cream 280 being directed generally radially through the slot in the direction shown, for example, by the arrows 177 and 177a. The interfacing portions of the extended side walls 84 and 85 are essentially identical dimensionally and structurally so that the cream 280 passing through the slot 80 is confined to the space between the parallel extended side walls. The slot 81 (FIG. 2), of the prior applicator 66, is arranged in the same manner as the slot 80, with the extended side walls 178a and 178b confining the passage of the cream 280 in the generally radial direction of the arrows 179 and 179a (FIG. 6a).

As shown in FIGS. 6 and 6a, the slots 176 and 178, of the second prior applicator 160, are essentially identical structurally, dimensionally, and spatially to the slots 176 and 178 of the first prior applicator 66, thereby to confine the passage of the cream 280 through the slots in the same manner as described above with respect to the slots of the first prior applicator 66.

Referring to FIGS. 6 and 6a, the slot 176 of the prior applicator 160 is formed with two extended side walls 176a and 176b, which are spaced, parallel, and interfacing, to define the opening of the slot, through which the cream 280 will pass. In this arrangement of the slot 176 of the prior applicator 160, the extended side wall 176a occupies a first location within the opening of the slot, and the extended side wall 176b occupies a second location within the opening of the slot. In the same manner, the slot 178 of the prior applicator 160 is formed with two extended side walls 178a and 178b, which ae spaced, parallel, and interfacing to define the opening of the slot. The extended side wall 178a occupies a first location within the slot 178, and the extended side wall 178b occupies a second location within the slot.

It is noted that the first prior applicator 66 and the second prior applicator 160 are being described above in, and illustrated in FIGS. 1 through 6, 6a and 6b of, this application to show the structure of prior applicators, particularly with respect to the structure of the slots, and adjacent structure, of the prior applicators such as disclosed, for example, in above-noted U.S. Pat. No. 7,141,036.

Referring now to FIGS. 7 through 16, and as described below, each of a first current applicator 270 (FIGS. 7, 8, 11, and 12), a second current applicator 271 (FIGS. 9, 10, 13, and 14), and a third current applicator 272 (FIGS. 15 and 16), include features which are described, claimed, and illustrated in this application, and include structure, and methods of use, which differ from the that of the above-described first prior applicator 66, and the second prior applicator 160, which are described and illustrated, but not claimed, in this application. The first, second, and third current applicators 270, 271, and 272, respectively, are identified as "current" applicators to identify the applicators which are described, claimed, and illustrated in this application, in comparison with the first and second "prior" applicators 66 and 160, respectively.

Some of the structure of the below-described first, second, and third current applicators 270, 271, and 272, respectively, is similar to corresponding structure of the above-described first and second prior applicators 66 and 160, respectively. Therefore, for consistency, some of the numeric, and the alpha-numeric, indicators for the structural features of the first and second prior applicators 60 and 160, which are common to corresponding structural features of each of the first, second, and third current applicators 270, 271, and 272, respectively, will be used to identify the corresponding structural features of the first, second, and third current applicators.

Figure 15:
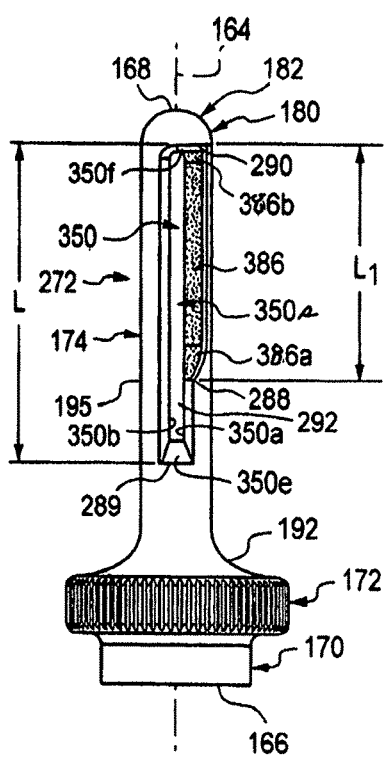
FIG. 15 is a front view of a third current applicator, as described, illustrated, and claimed in this application, with the flat surface of each slot extending along an axial portion adjacent the respective slot, from a location intermediate the proximal end and the distal end of the slot, to the distal end of the slot, in accordance with certain principles of the invention.

As shown in FIGS. 7, 8, and 15, each of the first, second, and third current applicators 270, 271, and 272, respectively, has an integrally-formed, unitary body 162, which extends along an axis, or centerline, 164 between a proximal end 166 and a closed distal end 168 of the body. The body 162 is formed integrally with (1) a proximal coupler 170 which extends axially from the proximal end 166 of the body, (2) a circular flange 172 which extends radially from the body 162, (3) an axially-elongated stem 174 formed transaxially with two axially-elongated diametrically-spaced slots 350 and 352, or cream passages, (4) an axially-elongated solid spacer 180, and (5) an axially-elongated dome 182 which extends axially to the distal end 168 of the body.

Also, as shown in FIGS. 9 through 14, and 16, the body 162 of each of the three current applicators 270, 271, and 272 is formed with the slot delivery passage 200 to provide a path for the forced feeding of the cream 280 (FIG. 12) into the proximal end 166 of each current applicator and toward the distal end 168 thereof. As the cream 280 is force-fed through the slot delivery passage 200 of each of the three current applicators 270, 271, and 272, respectively, the cream is force-fed through the entry 201, and the entry 203, of the slots 350 and 352, or cream passages, respectively, and into the respective slots. The cream 280 is then fed through the slots 350 and 352, or cream passages, to an exit 350s and an exit 352s, respectively, of each of the three current applicators 270, 271, and 272, in a manner to be described below, which is distinct in comparison to the feeding of the cream through the slots 176 and 178 of each of the two prior applicators 66 and 160.

In the following description of the structure and function of the slots 350 and 352 of the first, second, and third current applicators 270, 271 and 272, the cream passages of the slots will be described with respect to the two-dimensional illustrations of the drawings. The third dimensional factor of the volume of the cream passages, i.e., the slot length "L," (FIG. 15) is to be understood.

In the three current applicators 270, 271, and 272, as shown in FIGS. 1 through 14, each slot 350 and 352 is formed with exits 350s and 352s, respectively. The exit 350s is formed as a single opening with two exit-opening sections 350t and 350u. The exit-opening section 350t is aligned, in a direction of the transaxis 202, with the entry 201. The exit-opening section 350u is adjacent and contiguous with the exit-opening section 350t, with at least portions thereof not in transaxial alignment with the entry 201. The exit 352s is formed in a manner identical to the exit 350s, and includes two exit-opening sections 352t and 352u. The purpose and function of the exits 350s and 352s will be explained below.

As further shown in FIGS. 9 through 16, in each of the first, second, and third prior applicators 270, 271, and 272, the slot 350, or cream passage, is formed with a single extended side wall 350b, or extended barrier side wall, on one side only of the slot, and having the width "W." The extended barrier side wall 350b is the only extended side wall in the slot 350. As particularly shown in FIG. 9, the extended barrier side wall 350b occupies a location comparable to the above-mentioned second location within the slot 176 (FIG. 6), which is occupied by the extended side wall 176b of the second prior applicator 160. The location within the slot 350, which is comparable to the first location of the extended side wall 176a (FIG. 6) in the second prior applicator 160, is open, or partially open, both as described below, and does not include an extended side wall.

Figure 11:
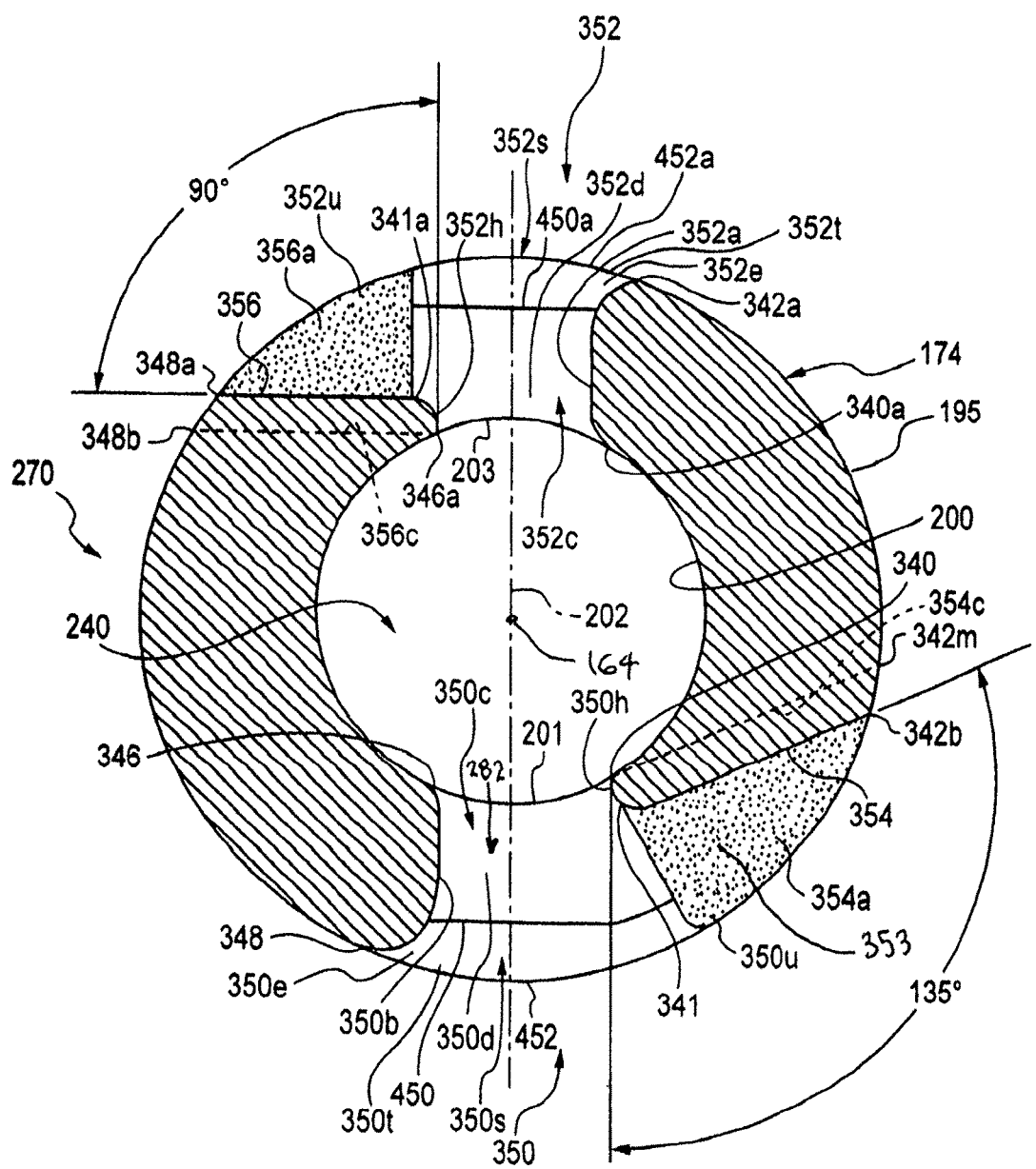
FIG. 11 is an enlarged view of the sectioned portion of the slot section of FIG. 10 showing different angular arrangements of the flat surfaces of the first current applicator, and further showing an abbreviated side wall of each slot, in accordance with certain principles of the invention.

Instead, as shown in FIG. 11, an abbreviated side wall 350h is formed in the slot 350 of the first current applicator 270, and is located in a plane comparable to the plane of the extended side wall 176a of the second prior applicator 160. Further, the abbreviated side wall 350h is formed with an inboard end at the integral juncture 340 with the slot delivery passage 200, and an outboard end at a juncture 341, where the abbreviated side wall is joined with an inboard end of an extended flat surface 354. The abbreviated side wall 350h and the extended flat surface 354 are located on a first side of the slot 350, and are spaced from (1) the extended barrier side wall 350b, which is located on a second side of the slot opposite the first side, and (2) the transaxis plane, which is coincidental with the transaxis 202.

The width of the abbreviated side wall 350h is less than the width "W," and is spaced inboard from the common external surface 195. In the illustration of FIG. 11, the abbreviated side walls 350h and 352h are each considerably less in width than the width "W" (FIG. 6a) as noted above, but could be greater than the width illustrated in FIG. 11, and still be less than the width "W," without departing from the spirit and scope of the invention.

Figure 12:
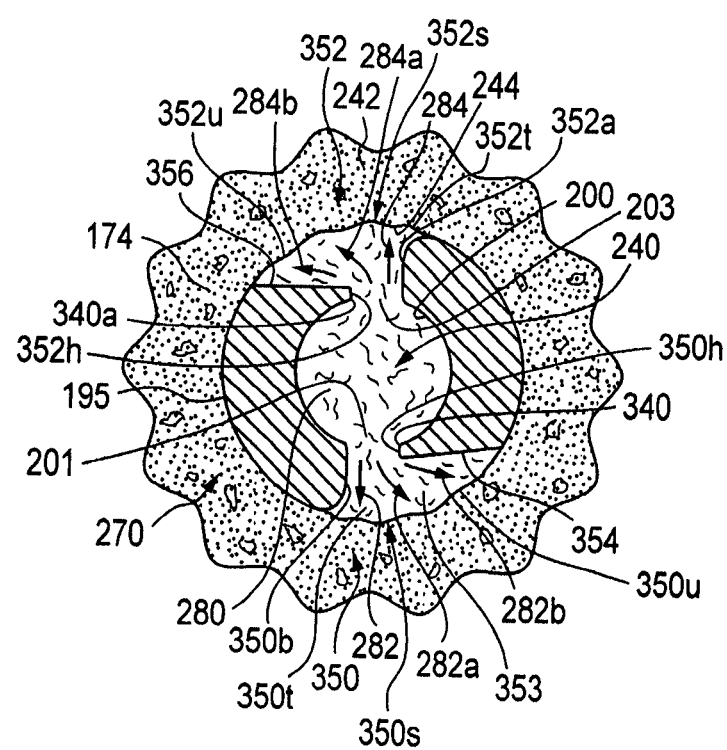
FIG. 12 is a sectional view showing the first current applicator of FIG. 11 located within a body opening of a patient, and the manner in which medicinal cream is applied to tissue within the body opening, including arrow-indicated flow-paths of the cream, relative to the abbreviated side wall and the openings of the two slots and the respective flat surfaces, in accordance with certain principles of the invention.

As shown in FIGS. 11 and 12, and as noted above, the inboard end of the extended flat surface 354 angularly joins with the outboard end of the abbreviated side wall 350h at a the juncture 341. The abbreviated side wall 350h extends from the inboard end thereof, at the juncture 340, outward to the juncture 341, from which the extended flat surface 354 extends angularly to a juncture 342b with the common external surface 195.

The extended flat surface 354 extends angularly outward from the juncture 341 to the juncture 342b with the common external surface 195 at a flat-surface angle with respect to the abbreviated side wall 350h. The extended flat surface 354 also extends away from, and in an angularly direction with respect to, the extended barrier side wall 350b, which, by virtue of the location of the slot 350, is spaced from the extended flat surface. Also, the extended flat surface 354 extends axially along the full axial length "L" of the slot 350.

Figure 13:
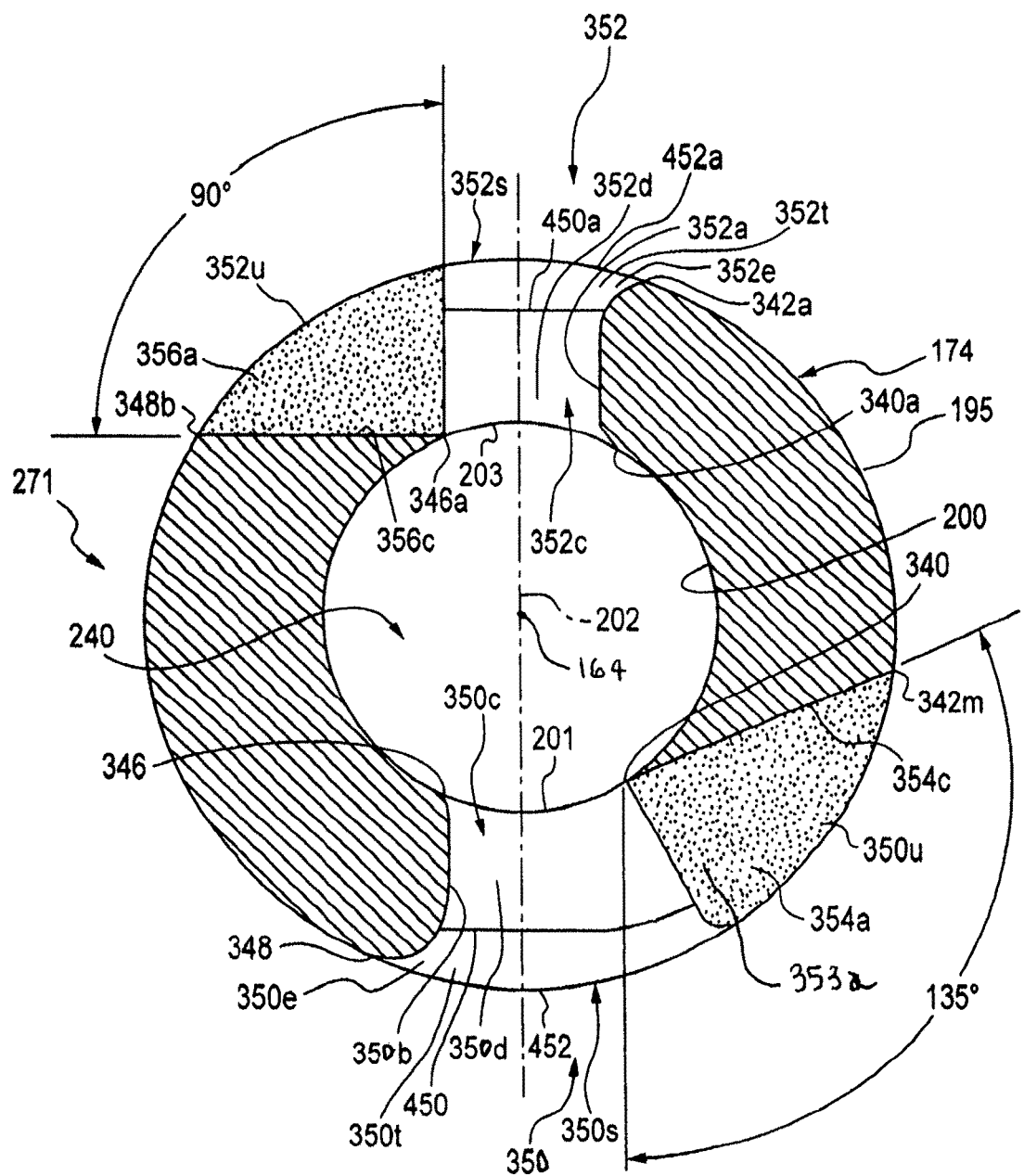
FIG. 13 is an enlarged view of the sectioned portion of the slot section of FIG. 10 showing a second current applicator, as described, illustrated, and claimed in this application, having different angular arrangements of flat surfaces of a second current applicator without the abbreviated side wall of each slot of FIG. 11, in accordance with certain principles of the invention.
Figure 16:
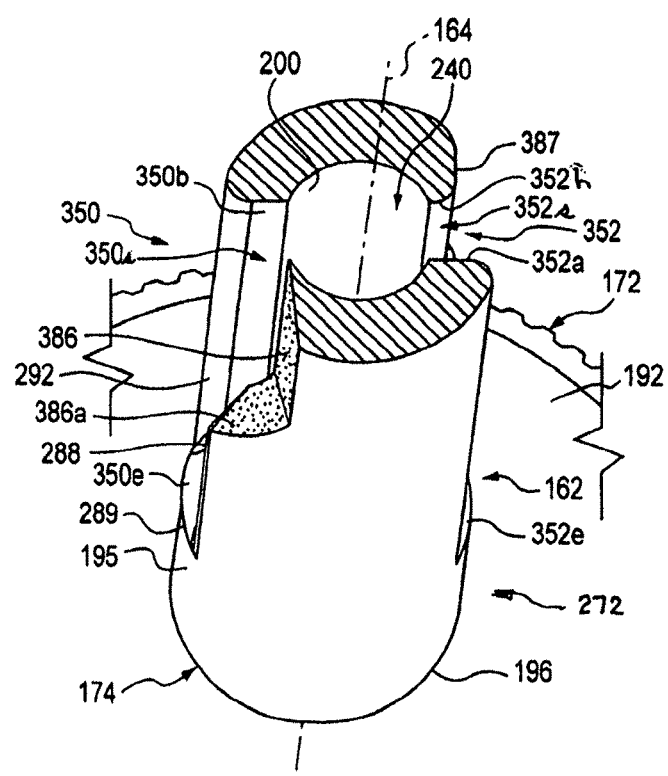
FIG. 16 is a partially-sectioned, perspective view showing a portion of the third current applicator of FIG. 15, with a slot section, or stem, of the body thereof being sectioned to show interior structure of the two slots in relation to the respective flat surfaces, in accordance with certain principles of the invention.

Note that in the third current applicator 272, as shown in FIGS. 15 and 16, an extended flat surface 386 does not extend the full axial length of the slot 350. However, the portion of the slot 350, which includes the axially-shorter extended flat surface 386, functions in the same manner as the slot 350 with the axially-longer extended flat surface 354 of the slot 350 of the first current applicator 270. In similar fashion, the slot 352 is arranged with a flat surface 387, which extends less than the full length "L" of the slot. It is noted that, without departing from the spirit and scope of the invention, the slots 350 and 352 of the third current applicator 272 could be formed with abbreviated side walls 350n and 352h, respectively, (FIG. 11), or without abbreviated side walls (FIG. 13). Further, the axially-shorter extended flat surfaces 386 and 387 (FIG. 16) could be formed with a proximal end located at the proximal end of the respective slots 350 and 352, and not extend to the respective distal ends of the slots, or could be formed with proximal and distal ends which are each spaced from the proximal and distal ends of the respective slots, without departing from the spirit and scope of the invention.

Figure 10:
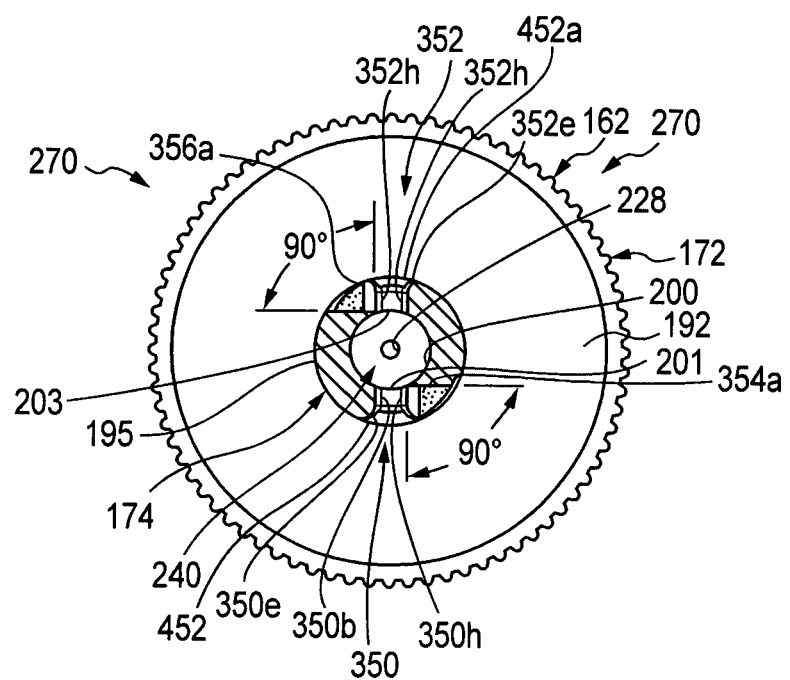
FIG. 10 is a section view taken along line 10-10 of FIG. 8, with a flange extracted from the sectional view for clarity purposes, to further show the angular relationship of the single extended side wall of each of the two slots and the respective flat surface, in accordance with certain principles of the invention.

As shown in FIG. 10, the flat-surface angle for the extended flat surface 354, with respect to the extended barrier side wall 350b is ninety degrees, but could be at angles less or greater than ninety degrees without departing from the spirit and scope of the invention. In one representative example of a different flat-surface angle, as shown in FIG. 11, the flat-surface angle of the extended flat surface 354 is one hundred and thirty-five degrees.

Figure 9:
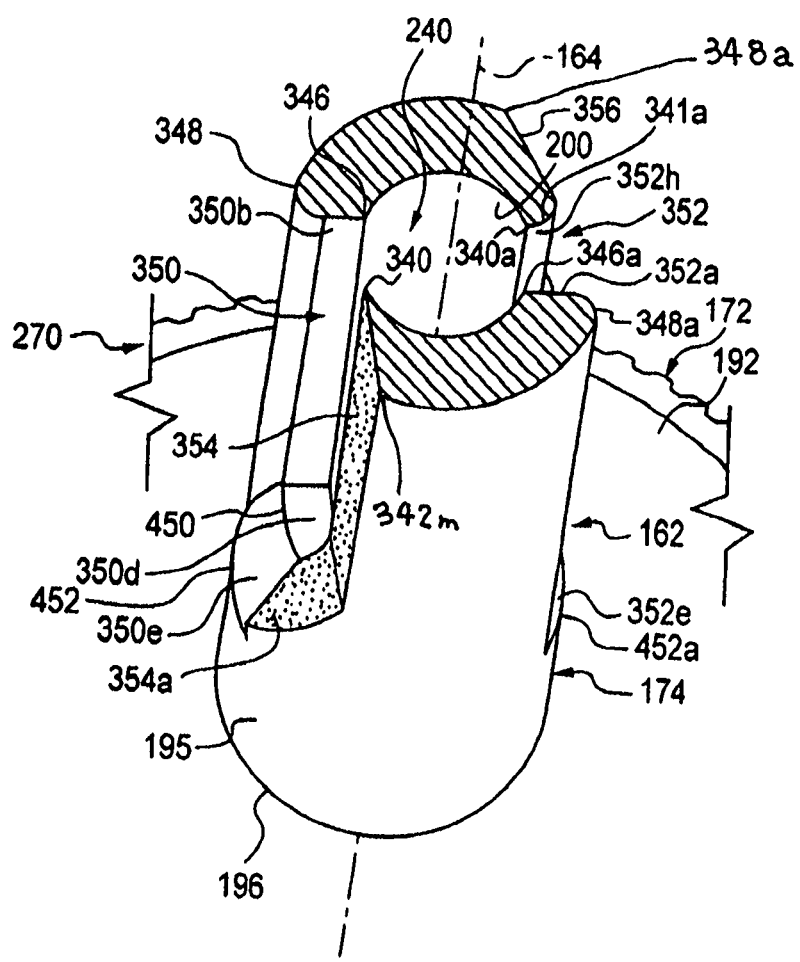
FIG. 9 is a partially-sectioned, perspective view showing a portion of the first current applicator of FIG. 7 with a slot section, or stem, of the body thereof being sectioned to show that the respective flat surface of each of the two slots extends angularly, laterally, away from the respective single extended side wall, and the transaxis plane, in accordance with certain principles of the invention.

As shown in FIGS. 7, 9 and 11, the first current applicator 270 is formed with a triangularly-shaped, proximal, flat transition surface 354a, which extends in a proximal direction and outward to the common external surface 195 from a proximal end of the extended flat surface 354, and is located adjacent a proximal transition surface 350e, or ramp. A similar triangularly-shaped, distal, flat, transition surface 354b (FIG. 7) extends in a distal direction and outward to the common external surface 195 from a distal end of the extended flat surface 354, and is located adjacent the distal transition surface 350f (FIG. 8). The proximal and distal flat transition surfaces 354a and 354b, respectively, form proximal and distal portions, respectively, of, and are thereby included in, the extended flat surface 354.

Referring again to FIG. 11, the first current applicator 270 is formed with an extended flat surface 356, and an abbreviated side wall 352h spaced from, and generally parallel with, the extended side wall 352b, which is the only extended side wall associated with the slot 352. As shown in FIG. 11, the abbreviated side wall 352h is formed with an inboard end at the integral juncture 346a with the slot delivery passage 200, and an outboard end at a juncture 341a with the extended flat surface 356. The inboard end of the extended flat surface 356 is located on one side of the slot 352, and is spaced from the extended side wall 352a, which is located on the opposite side of the slot.

The width of the abbreviated side wall 352h is less than the width "W," and is spaced inboard from the common surface 195. The extended flat surface 356 is contiguous angularly with the abbreviated side wall 352h at the juncture 341a of the extended flat surface and the outboard end of the abbreviated side wall. The abbreviated side wall 352h extends from the inboard end thereof, at the juncture 340a, outward to the juncture 341a, from which the extended flat surface 356 extends to a juncture 348a with the common external surface 195.

The extended flat surface 356 extends angularly outward from the juncture 341a to the juncture 348a with the common external surface 195, at a flat-surface angle with respect to the abbreviated side wall 352h. The extended flat surface 356 also extends away from, and in an angularly direction with respect to, the extended side wall 352a, which, by virtue of the location of the slot 352, is spaced from the extended flat surface. Also, the extended flat surface 356 extends axially along the full axial length "L" (FIG. 15) of the slot 352.

In the illustration of FIG. 11, the abbreviated side wall 352h is considerably less in width than the width "W" (FIG. 6a), but could be greater than the width thereof illustrated in FIG. 11, and still be less than the width "W," without departing from the spirit and scope of the invention.

As noted above, the triangularly-shaped, proximal, flat transition surface 354a extends from a proximal end of the extended flat surface 354 and outward, in a proximal direction, to the common external surface 195. A similar triangularly-shaped, distal, flat transition surface 354b (FIG. 7) extends in a distal direction and outward to the common external surface 195.

In the manner described above, the extended flat surface 354, including the proximal and distal transition surfaces 354a and 354b (FIGS. 7 and 8), respectively, extends the axial length "L" (FIG. 15) of the slot 350, i.e., as noted above and shown in FIGS. 7 and 8, between (1) the proximal juncture 452 of the proximal transition surface 350e and (2) the distal juncture 456 of the distal transition surface 350f (FIG. 7), with the common external surface 195.

Similarly, as shown in FIG. 8 and as described above, the extended flat surface 356, including the transition surface 356a and the transition surface at the distal end of the slot, extends the axial length "L" (FIG. 15) of the slot 352, i.e., as noted above, between (1) the proximal juncture 452a of the proximal transition surface 352e with the common external surface 195 and (2) the distal juncture 456a of the distal transition surface 352f with the common external surface.

Referring to FIG. 12, the cream 280 is provided from a supply of the cream, as described above, and exits from the chamber 240, of the first current applicator 270, and enters the slot 350 through entry 201, and into the cream passage of the slot. The cream 280 is immediately confined between the extended barrier side wall 350b and the spaced, parallel, abbreviated side wall 350h, thereby urging the cream through the cream passage, in the direction of the arrow 282, and precluding any lateral movement thereof. Subsequently, the cream passes the abbreviated side wall 350h and a first portion of the cream continues in the direction of the arrow 282, due to the continued barrier presence of the extended barrier side wall 350b, and towards a first location, i.e., the exit-opening section 350t of the exit 350s, and onto a first cream-receptive surface.

The entry 201 is formed with a prescribed size and the exit 350s is larger than the prescribed size. The exit 350s is formed with a first open portion, i.e., exit-opening section 350t, and a second open portion, i.e., exit-opening section 350u, which is contiguous with the first open portion.

With the cream 280 having been moved past the abbreviated side wall 350h (FIG. 11), a second portion of the cream 280 is allowed to, and does, flow laterally, angularly of the flow direction of the first portion of the cream, and of the extended barrier side wall 350b, into an enlarged chamber 353, which is an enlarged portion of the cream passage resulting from the formation, and flat-surface angle, of the flat surface 354. The enlarged chamber 353, which extends the length "L" (FIG. 15) of the slot 350, provides a cream passage volume which is greater than the above-noted prescribed volume of the cream passage of the slots 176 and 178 of the second prior applicator 160. Eventually, the cream 280 passes angularly through the chamber 353, over the flat surface 354, towards and through the exit-opening section 350u of the exit 350s and is applied, or spread, angularly onto exposed surfaces of the tissue 242 of the patient, i.e., a second cream-receptive surface, adjacent and contiguous with the first cream-receptive surface.

Referring further to FIG. 12, the above described structure of the slot 350 and the flow path of the cream 280 therethrough applies equally to the structure of the slot 352 and the flow path of the cream therethrough.

Referring to FIG. 13, without departing from the spirit and scope of the invention, in the second current applicator 271, there is no abbreviated side wall in the location previously occupied by the abbreviated side wall 350h (FIG. 11) described above, and the location is open. Instead, an inboard end of an extended flat surface 354c (also shown in dashed line in FIG. 11) is located at the juncture 340 thereof with the slot delivery passage 200, and extends outward from the juncture toward, and to, a juncture 342m at the common external surface 195. As noted above, the second current applicator 271 does not include the abbreviated side wall 350h (FIG. 11), or any side wall in place thereof.

In similar fashion, without departing from the spirit and scope of the invention, in the second current applicator 271, and with respect to the slot 352, an inboard end of an extended flat surface 356c is located at the juncture 346a thereof with the slot delivery passage 200, instead of being located at the outboard end of an abbreviated side wall. In the second current applicator 271, the extended flat surface 356c extends outward from the juncture 346a toward, and to, a juncture 348b at the common external surface 195. In the same above-described manner regarding the slot 350 of the first current applicator 270, the slot 352 of the second current applicator 271 will not include an abbreviated side wall, or any side wall in place thereof.

Figure 14:
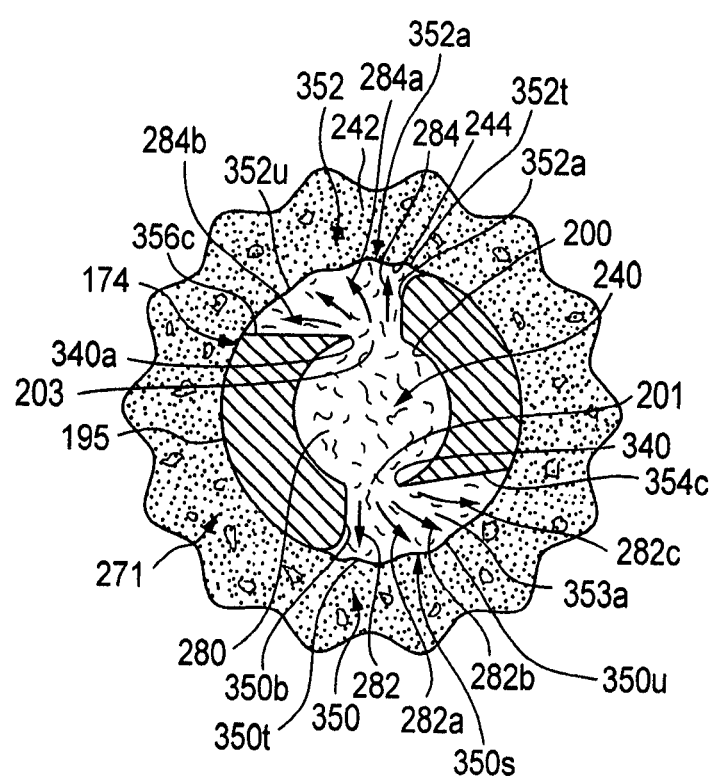
FIG. 14 is a sectional view showing the second current applicator of FIG. 13 located within a body opening of a patient, and the manner in which medicinal cream is applied to tissue within the body opening, including the arrow-indicated flow-paths of the cream, relative to the openings of the two slots, without abbreviated side walls, and the respective flat surfaces, in accordance with certain principles of the invention.

Referring to FIG. 14, the cream 280 exits from the chamber 240, of the second current applicator 271, and enters the slot 350 through entry 201, and into the cream passage of the slot. A first portion of the cream 280 is immediately confronted by the extended barrier side wall 350b precluding the cream from moving in a direction into the extended barrier wall, thereby urging the cream, through the cream passage, in the direction of the arrow 282. The first portion of the cream continues in the direction of the arrow 282, due to the continued presence of the extended barrier side wall 350b, and directly towards, and through, the exit-opening section 350t of the exit 350s and onto prepositioned, exposed, first portion of the surfaces of the tissue 242 of the patient.

A second portion of the cream 280, which enters the entry 201 of the slot 350 with the first portion thereof, is allowed immediately to, and does, flow into an enlarged chamber 353a of the cream passage resulting from the formation, and selected flat-surface angle, of the flat surface 354c. The enlarged chamber 353a, which extends the length "L" (FIG. 15) of the slot 350, provides a second cream passage volume which is greater than the above-noted prescribed volume, and is also greater than the above-noted first cream passage volume. Eventually, the cream 280 passes through the chamber 353a in the direction of arrows 282a, 282b, and 282c, over the flat surface 354c, towards and through the exit-opening section 350u of the exit 350s and onto prepositioned, exposed surfaces of the tissue 242 of the patient. Note that fourth arrow 282d reflects the additional volume of the chamber 353a over the volume of the chamber 353.

By forming the flat surface 354c directly from the junction point 340, and extending the flat surface at a selected flat-surface angle, the second portion of the cream 280 immediately moves into the chamber 353a, which is larger than the chamber 353 (FIG. 12), and passes through the chamber as noted above. By virtue of the direction of movement of the second portion of the cream 280 as noted above, the cream approaches the surface of the tissue 242 at an angle, resulting in the second portion of the cream being spread onto the surface of the tissue rather than being fed directly onto the surface of the tissue 242 in the manner of the first portion of the cream.

As shown in FIGS. 12 and 14, the stem 174 of the first current applicator 270 is located within the body opening 244 of the patient, with the illustration looking outward from within the opening. The cream 280 enters the chamber 240, then, as described above, passes through the slots 350 and 352, and is applied to exposed surfaces of the tissue 242 adjacent exits 350s and 352s, respectively, of the slots.

Thus, the structure of the second current applicator 271, as described above, facilitates selective placement, with selective different amounts, of the cream 280 onto different portions of the surfaces of the tissue 242.

Referring to FIG. 15, the abbreviated flat surfaces 386 and 387 of the third current applicator 272 could be placed at any of many locations along the axial length "L" (FIG. 15) of the slots 350 and 352, respectively., with a length, such as, for example, "$L_1$" (FIG. 15) which is less than the axial length "L" without departing from the spirit and scope of the invention. For example, the respective proximal ends of the abbreviated flat surfaces 386 and 387 could be located at the proximal ends of the slots 350 and 352, respectively, and the distal ends thereof located at the above-noted intermediate points (FIGS. 13 and 14) of the respective slots. In another example, two or more axially spaced sections of abbreviated flat surfaces 386 could be located along the slot 350, and two or more axially spaced abbreviated flat surfaces 387 could be located along the slot 352. Or, for example, the proximal ends of the abbreviated flat surfaces 386 and 387 could be spaced distally from the proximal ends of the slots 350 and 352, respectively, and the distal ends of the abbreviated flat surfaces could be spaced from the respective distal ends of the slots. Further, for example, the abbreviated flat surfaces 386 and 387 could be at different radial positions along the respective slots 350 and 352, and, therefore, not radially aligned. Additionally, for example, the abbreviated flat surfaces 386 and 387 could be formed at different flat-surface angles in the manner illustrated in FIGS. 11 and 13.

In the above-described first, second, and third current applicators 270, 271, and 272, the surfaces 354, 354c, 356, 356c, 386, and 387 are flat, but could be other than flat, such as, for example, at least portions of the surfaces being formed with peaks, depressions, undulations, being concave or convex, or the like, without departing from the spirit and scope of the invention.

Each of the above-described three current applicators 270, 271, and 272 is described and illustrated as being formed with two slots each; however, each of the applicators could be formed with a single slot, or more than two slots, all without departing from the spirit and scope of the invention.

Figure 21:
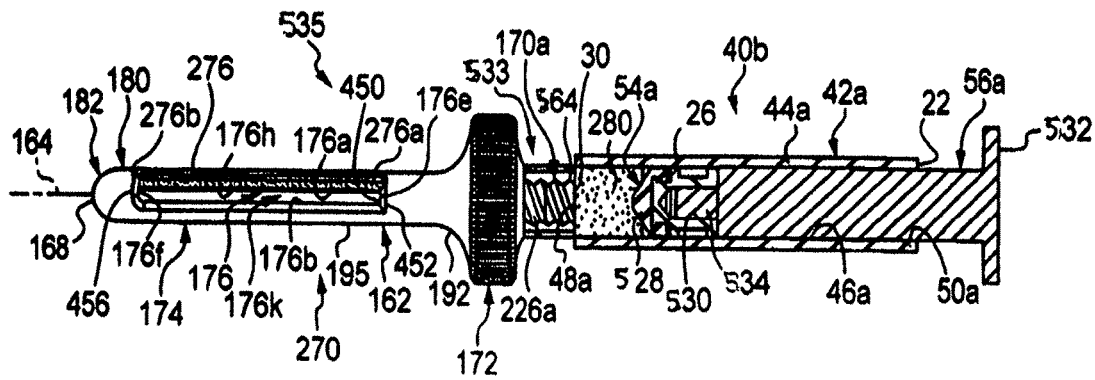
FIG. 21 is a sectional view showing a stem having a distal end assembled with the proximal end of the plunger partially within the substance-loaded barrel to form a syringe, which is in assembly with an applicator having slots along the side thereof, to form a syringe/applicator assembly, in accordance with certain principles of the invention.
Figure 22:
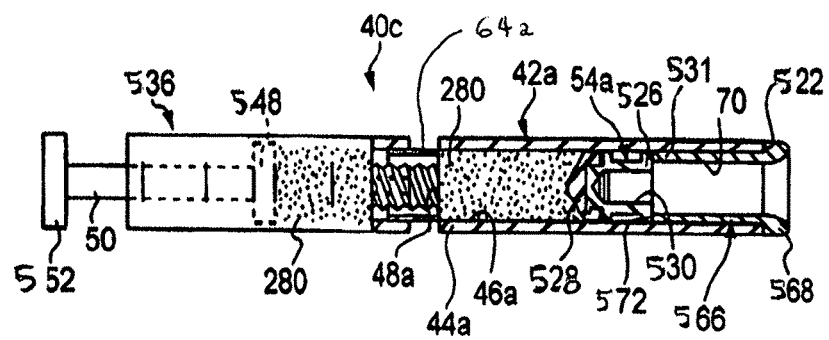
FIG. 22 is a sectional view showing the substance loading device, such as the squeeze tube of FIG. 19, having loaded the substance into the barrel, to urge the plunger into engagement with a stop surface formed by the distal end of a guide located within the proximal end of the barrel, in accordance with certain principles of the invention.
Figure 23:
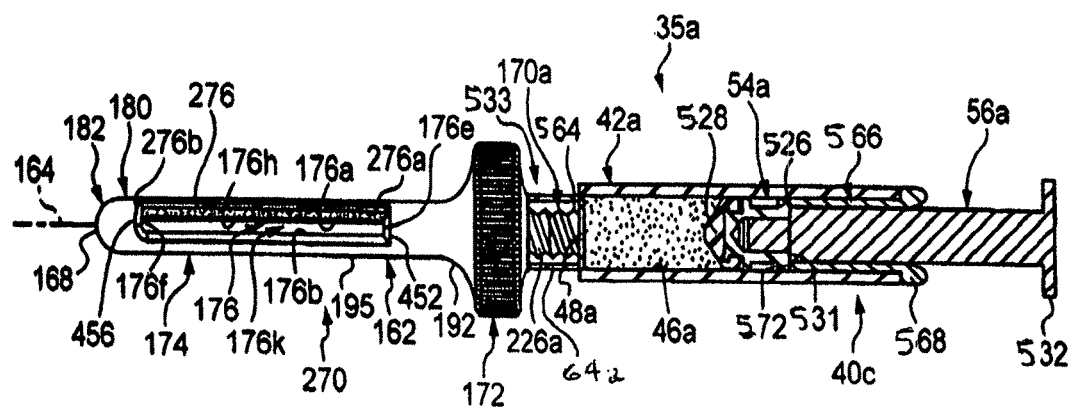
FIG. 23 is a sectional view showing a syringe/applicator assembly, including the stop surface of FIG. 22, prepared for dispensing the barrel-contained substance, in accordance with certain principles of the invention.

Referring to FIGS. 21 through 23, described below are various methods of preparing the cream-loaded syringes 40b and 40c, with the applicator 270, to form cream delivery assemblies 535 (FIGS. 21) and 535a (FIG. 23) for use in the application of a substance, such as, for example, the cream 280, onto body surfaces of a patient, such as, for example, the tissue 242 within the body opening 244 of the patient, as shown in FIG. 12.

As noted above, and as shown in FIGS. 1 and 3, the syringe 40 includes the cartridge 42 formed with the barrel 44 having the hollow, open-ended, barrel passage 46 extending axially therethrough. The cartridge 42 also includes, at its distal end, the axially open, internally unthreaded sleeve 64. The syringe 40, which is formed with the frictional coupling assembly 45 (FIG. 3), differs primarily from each of the syringes 40b (FIGS. 21) and 40c (Fig, 23), which are formed with a threaded coupling assembly, such as, for example, a sleeve 64a having a threaded axial passage 520 (FIG. 17), which is in axial communication with a barrel passage 46a.

As shown in FIGS. 21 and 23, the syringes 40b and 40c, respectively, are similar in structure to the syringe 40 (FIG. 1), which is described above. Each of the syringes 40b and 40c include a cartridge 42a having a barrel 44a with the hollow, open-ended, barrel passage 46a extending axially therethrough. The cartridge 42a also includes, at its distal end, the axially open, internally threaded sleeve 64a. The sleeve 64a has proximal and distal openings and a threaded axial passage 520 (FIG. 17), which is threaded, and in axial communication with the barrel passage 46a.

Figure 17:
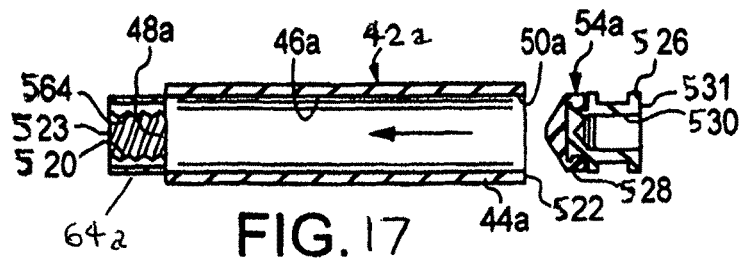
FIG. 17 is a sectional view showing a plunger located spatially from a proximal end of a barrel of a cartridge, in accordance with certain principles of the invention.

As shown in FIG. 17, at a transaxial juncture of the distal end of the barrel 44a and the proximal end of the sleeve 64a, the diameter of a proximal opening 48a of the sleeve is smaller than the diameter of the barrel passage 46a, resulting in the formation of a wall 49 at the transaxial juncture. When the plunger 54a is moved in a distal direction within the barrel passage 46, the wall 49 functions as a stop to preclude travel of the plunger, in a distal direction, axially beyond the wall. The barrel 44a is formed with a proximal opening 50a at a proximal end 522 of the cartridge 42a, and the sleeve 64a is formed with a distal opening 523 (FIG. 17), whereby the cartridge is formed with a continuously open axial passage from, and through, the proximal opening 50a to, and through, the distal opening 523.

Referring further to FIGS. 21 and 23, each of the syringes 40b and 40c includes a two-piece plunger 54a formed by a plastic proximal portion 526 and a compliant distal portion 528, which are assembled and secured together. The plastic proximal portion 526 is formed with a proximal opening 530, and with a proximal end 531.

Each of the syringes 40a (FIGS. 21) and 40b (FIG. 23) includes a stem 56a having a flange-like thumb piece or stem depressor 532 at a proximal end thereof, and an axial coupling projection 534 at a distal end thereof, which fits into, and is retained within, the proximal opening 530 (FIG. 17) of the plastic proximal portion 526 of the plunger 54a.

Figure 19:
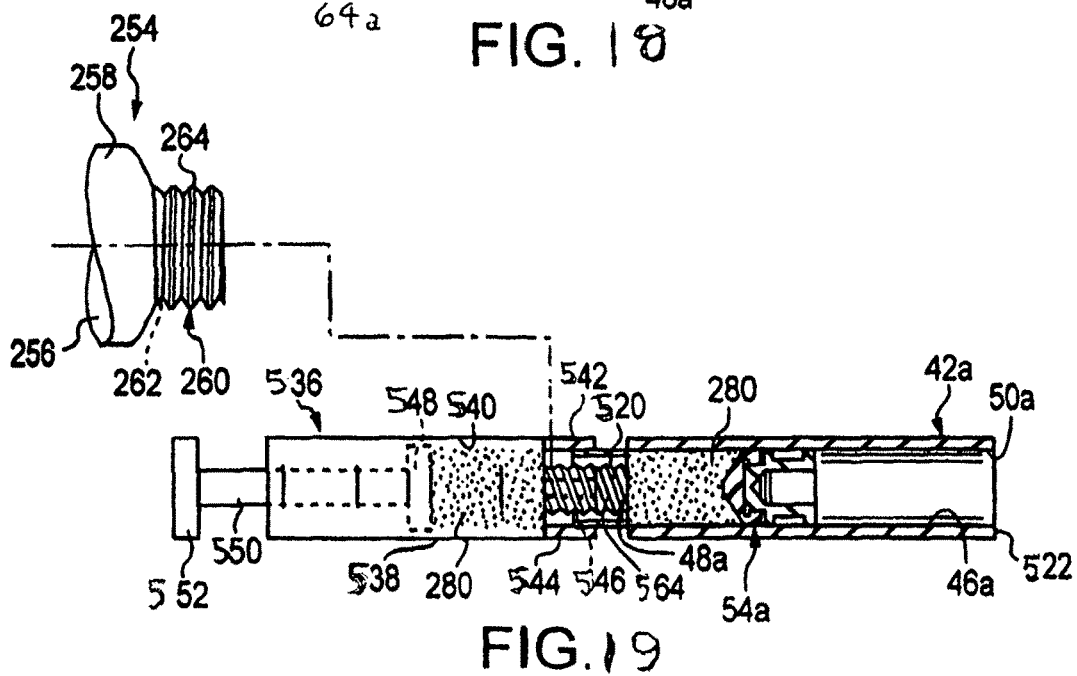
FIG. 19 is a partial sectional view showing a substance loading device, and alternately a squeeze tube, in assembly with the distal end of the barrel of FIG. 17 with the plunger head being urged away from the distal end of the barrel by the substance being deposited into the barrel, in accordance with certain principles of the invention.

As shown in FIG. 19, a syringe-like cream-supply container or dispenser 536 can be used to load the cream 280 (FIG. 12) into the cartridge 42a as described below. The dispenser 536 includes a barrel 538 formed with an axial, open ended, barrel passage 540, with a sleeve 542 extending from a distal end of the barrel. An externally threaded nipple 544 extends axially from the distal end of the barrel 538, and is located concentrically within the sleeve 542. The nipple 544 is formed with an axial passage 546, which is in communication with the barrel passage 540, so that cream located within the barrel passage 540 can flow through, and out of the distal end of, the axial passage 546. Also, the dispenser 536 includes a cream pusher head 548, which is attached to a distal end of a stem 550, and which is located within the barrel passage 540. A thumb piece or depressor 552 is attached to a proximal end of the stem 550, and is located outside of, and spaced from, a proximal end of the barrel 538. In use, a supply of the cream 280 (FIG. 12) will be contained within the barrel passage 540 of the dispenser 536, between the distal end of the barrel passage 540 and a distal side of the pusher head 548. By pressing on the depressor 552, the cream 280, within the barrel 538, will be moved into the barrel 44a to move or force the plunger 54a in a proximal direction within the barrel passage 46a.

A squeeze-tube cream-supply container or dispenser, such as the squeeze tube 254 (FIG. 19), can be used as an alternative to the syringe-like dispenser 536 to load the cream 280 into the syringe 40b or 40c, as described below. The squeeze tube 254 includes an enclosure 256 formed by a flexible wall 258 with a single-outlet nipple 260 having an axial outlet passage 262 formed therethrough, which communicates with the enclosure. The exterior of the nipple 260 is formed with threads 264. By squeezing the squeeze tube 254, the cream 280, within the barrel 538, will be moved into the barrel 44a to move or force the plunger 54a in a proximal direction within the barrel passage 46a.

Figure 18:
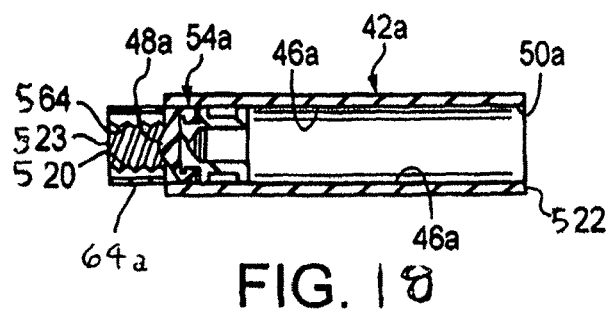
FIG. 18 is a sectional view showing the plunger head of FIG. 17 assembled within, and located at the distal end of, the barrel of FIG. 17, in accordance with certain principles of the invention.

In another cream-loading process as illustrated in FIG. 22, prior to the loading of the cream 280 into the barrel passage 46a, and after the plunger 54a has been placed into the barrel passage, as shown in FIG. 18, a guide 566, as shown in FIGS. 22 and 23, is inserted into the proximal opening 50a of the barrel passage until a flange 568 of the guide engages the proximal end 522 of the cartridge 42a. The guide 566 is formed with an open-ended axial passage 570, through which a stem 56b is moved and guided. The guide 566 is formed with a stop surface 572 at the distal end of the guide. The stop surface 572 is located to engage the proximal end 531 of the plunger 54a, as the plunger is moved in a proximal direction, by virtue of the force of the incoming cream 280 being loaded into the barrel passage 46a. This action limits the proximal travel of the plunger 54a and, thereby, the volume of the cream 280 that can be loaded into the barrel passage 46a.

Referring to FIGS. 21 and 23, it is noted that a squeeze tube 254 could be used in place of the syringe 40b, with a threaded coupling assembly 533, to form the cream delivery assemblies 535 and 535a, without departing from the spirit and scope of the invention.

As noted above, several methods of loading an initial volume of the cream 280 into the cartridge 42a are described below, and with reference to FIGS. 17 through 23. A first of such methods includes the steps of (1) initially providing the cartridge 42a, having the barrel 44a, the barrel passage 46a and the sleeve 48a with the threaded axial passage 520, (2) inserting the plunger 54a into the barrel passage 46a from the proximal end 522 of the cartridge, (3) locating the distal end of the plunger at a distal end of the barrel passage 46a, (4) depositing the initial volume of the substance or cream 280 into the axial passage 520 through the distal opening 523 at the distal end of the cartridge, and into the barrel passage; and (5) moving the plunger in a proximal direction within the barrel passage, toward the proximal end of the cartridge, by a force of the initial volume of the substance being deposited into the distal passage.

A second method, which includes the steps of the first method described above, of loading an initial volume of the cream 280 into the cartridge 42a, and further includes the steps of (1) coupling the applicator 270 to the syringe 40b at the distal opening 523 of the sleeve 48a, (2) coupling the projection 534 of the stem 56a to the plunger 54a, and (3) moving the stem, and thereby the plunger, toward the distal end of the cartridge to urge at least some of the cream 280 from the barrel passage, and into the applicator 270.

A third method, which includes the steps of the first method described above, of loading an initial volume of a substance into the cartridge 42a, further includes the step of providing the stop surface 572 (FIGS. 22 and 23) within the barrel passage 46a at a location at which the plunger 54a is to be located when the initial volume of the cream 280 has been deposited into the barrel passage. Upon depositing the cream 280 into the barrel passage 46a, the force of the initial volume of the cream moves the plunger 54a to a location where a proximal end of the plunger is moved into engagement with the stop surface 572 to preclude further depositing of the cream into the barrel passage.

A fourth method, which includes the steps of the first method described above, of loading an initial volume of a substance into the cartridge 42a, further includes the step of providing the stop surface 372 (FIGS. 27 and 28) within the barrel passage 46a at a location at which the plunger 54a is to be located when the initial volume of the cream 280 has been deposited into the barrel passage, where, upon depositing the cream into the barrel passage, the force of the initial volume of the cream moves a proximal end of the plunger into engagement with the stop surface to preclude further depositing of the cream into the barrel passage.

Figure 20:
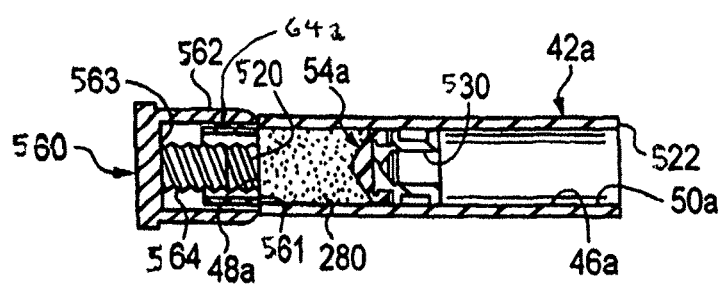
FIG. 20 is a partial sectional view showing the dispensing end of the loaded barrel of FIG. 17 being closed by a cap, in accordance with certain principles of the invention.

Referring to FIG. 20, a cap 560 is formed with an axially open end 561 at one end thereof, with an axially closed end 563 at the opposite end thereof, and forms a removable protective cylindrical shell 562. A threaded projection 564 extends concentrically within the shell 562 from an inner wall of the closed end 563. After the cream 280 has been loaded into the barrel passage 46a of the cartridge 42a, the cap 560 is manipulated to insert the threaded projection 564 into the threaded axial passage 520 of the axially open sleeve 48a of the cartridge 42a, to retain the cream 280 within the barrel passage 46a between the cap and the plunger 54a.

The cap 560 may also be used to retain any cream 280 remaining within the barrel passage 46a between successive applications of the cream onto tissue 242 of the patient, in the event that the applicator 270 is removed from assembly with the syringe 40b between such successive applications of the cream.

In general, the above-described various embodiments, as illustrated in the drawings of this application, are not to be construed as limiting the breadth of the present invention. Modifications, and other alternative constructions, will be apparent which are within the spirit and scope of the invention as defined in the appended claims.

What is claimed is:

1. An applicator for dispensing a medicinal substance therethrough, where the substance has a cream-like consistency of the type which does not flow without a force being applied thereto, which comprises:

a body formed about an axis which extends from a proximal end of the body to an exterior axial surface of a closed distal end of the body;

the body formed with a proximal section which extends from the proximal end of the body toward the closed distal end of the body, and to a distal end of the proximal section;

the proximal section of the body formed with an axial entry passage extending through the proximal section from a the proximal end of the body toward a the closed distal end of the body, and to a distal end of the axial entry passage;

the axial entry passage being formed with a prescribed diameter at the proximal end of the body;

the body being formed with an axial intermediate passage having a proximal end in communication with the distal end of the axial entry passage, and extending toward the closed distal end of the body, and to a distal end of the axial intermediate passage;

the axial intermediate passage being formed with a uniform passage diameter which is less than the prescribed diameter;

the body being formed about the axis thereof with a passage section, having a uniform exterior diameter, which extends from a proximal end thereof toward the closed distal end of the body, and to a distal end of the passage section;

the passage section of the body fully surrounding at least a portion of the axial intermediate passage to the distal end of the axial intermediate passage;

the body being formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section;

a slot delivery passage formed axially through the slot section of the body from a proximal end thereof toward the closed distal end of the body, and to a closed distal end of the slot delivery passage, with the proximal end of the slot delivery passage being in communication with the distal end of the axial intermediate passage;

at least one axially-elongated slot formed radially through the slot section of the body in unobstructed communication with the axial slot delivery passage and an external surface of the body, and extending from the proximal end of the slot section toward the distal end of the slot section, and to a distal end of the at least one axially-elongated slot;

the slot delivery passage being formed with the uniform passage diameter interrupted only by the presence of the at least one axially-elongated slot;

the at least one elongated slot formed with an extended side wall which extends axially from a proximal end to the distal end of the at least one elongated slot;

the extended side wall located at one side of the at least one elongated slot, and extending from an inboard juncture of the extended side wall with the slot delivery passage to an outboard juncture of the extended side wall with the external surface of the body;

a flat surface formed in the body adjacent the at least one elongated slot, having a first end spaced from the extended side wall, the flat surface extending from the first end thereof angularly away from the extended side wall to a second end of the flat surface at a juncture with the external surface of the body, and the flat surface extending axially along at least a portion of the at least one elongated slot.

2. The applicator as set forth in claim 1, which further comprises:

the body formed with a solid section, having the uniform exterior diameter, which extends from a closed proximal end of the solid section toward the closed distal end of the body, and to a closed distal end of the solid section, with the closed proximal end of the solid section being formed integrally with the distal end of the slot section.

3. The applicator as set forth in claim 2, which further comprises:

the body formed with a dome section in the form of a solid dome, which extends from a closed proximal end of the dome section to a closed distal end of the dome section, which is coincidental with the exterior axial surface of the closed distal end of the body;

the closed proximal end of the dome section being formed integrally with the closed distal end of the solid section; and the solid section and the dome section being exclusive of any opening.

4. The applicator as set forth in claim 1, which further comprises:

the flat surface extending from the first end thereof located at a juncture of the slot delivery passage and the at least one elongated slot and angularly away from the extended side wall to the second end of the flat surface at a juncture with the external surface of the body.

5. An applicator for dispensing a medicinal substance therethrough, which comprises:

a body formed about an axis with the body extending from a proximal end thereof to a distal end thereof;

a stem which forms an axial portion of the body;

the stem formed with a common external surface;

a slot delivery passage formed axially through at least a portion of the stem along an axis of the slot delivery passage;

a slot formed through a portion of the stem from the slot delivery passage to the common external surface to facilitate the flow of the medicinal substance from within the slot delivery passage, through the slot, and to an environment adjacent the common external surface;

the slot formed with a first side and a second side spaced from the first side;

an extended side wall, located at the first side of the slot, which is spaced from, and parallel with, a transaxis plane coincidental with a transaxis extending radially from the axis of the slot delivery passage and through the slot;

the extended side wall extending from an inboard juncture of the extended side wall with the slot delivery passage to an outboard juncture of the extended side wall with the common external surface of the stem;

a flat surface formed in the stem at the second side of the slot, having a first end spaced from the extended side wall and the transaxis plane;

the flat surface extending from the first end thereof in a direction angularly away from the extended side wall and the transaxis plane to a second end of the flat surface at a juncture with the common external surface of the stem, and the flat surface and the extended side wall extending axially along at least a portion of the slot.

6. The applicator as set forth in claim 5, which further comprises:

a floor formed in the stem adjacent an axial end of the slot, and forming a wall of the slot; and the floor being contiguous with the extended side wall, and extending from the extended side wall in a direction toward the first end of the flat surface.

7. The applicator as set forth in claim 6, which further comprises:

at least a portion of the floor being contiguous with, and extending toward the common external surface from, the flat surface.

8. The applicator as set forth in claim 5, which further comprises:

the flat surface extending along an entire axial length of the slot.

9. The applicator as set forth in claim 5, which further comprises:

the flat surface extending along a portion of an axial length of the slot from one end of the slot toward an opposite end of the slot, and to an intermediate location along the axial length of the slot.

10. The applicator as set forth in claim 5, which further comprises:

the flat surface extending along a portion of an axial length of the slot from a first intermediate location spaced from one end of the slot toward an opposite end of the slot, and to a second intermediate location along the axial length of the slot which is spaced from the first intermediate location.

11. The applicator as set forth in claim 5, which further comprises:

the first end of the flat surface extending from an inboard juncture thereof with the slot delivery passage to an outboard juncture of the second end of the flat surface with the common external surface.

12. The applicator as set forth in claim 6, which further comprises:

a mouth of the slot located at an intersection of a wall of the slot delivery passage and the floor, with the mouth extending between a first side thereof at the intersection and a second side thereof at the intersection, spaced from the first side, with a space between the first side and the second side defining an opening of the mouth at the intersection; and the first end of the flat surface located at the second side of the mouth, with the flat surface extending to the juncture with the common external surface.

13. The applicator as set forth in claim 5, which further comprises:

the axial length of the slot and the axial length of the slot delivery passage being the same.

14. An applicator for dispensing a substance therethrough, which comprises:
- a stem formed about an axis;
- a slot delivery passage extending through the stem along at least a portion of the axis;
- a common external surface formed on an exterior of the stem;
- a slot formed through the stem from, and through, the slot delivery passage to, and through, the common external surface, along a transaxis extending radially from the axis and through the slot;
- an extended side wall formed in the stem, which forms one side of the slot and is generally parallel with, and spaced from, a transaxis plane coincidental with the transaxis; and
- an angular surface formed in the stem, on a side of the slot opposite the one side thereof, which is spaced, and extends angularly away, from the extended side wall and the transaxis plane.

15. The applicator as set forth in claim 14, which further comprises:
- the angular surface formed in the stem extends angularly away from the transaxis.

16. An applicator for dispensing a medicinal substance therethrough, which comprises:
- a stem formed about an axis;
- a slot delivery passage extending through the stem along at least a portion of the axis;
- a common external surface formed on an exterior of the stem;
- a slot formed through a portion of the stem from the slot delivery passage to the common external surface to facilitate the flow of the medicinal substance from within the slot delivery passage, through the slot, and to an environment adjacent the common external surface;
- the slot formed with a first side and a second side spaced from the first side;
- an extended side wall, formed in the stem at the first side of the slot, which is spaced from, and parallel with, a transaxis plane coincidental with a transaxis extending radially from the axis and through the slot;
- the extended side wall extending from an inboard juncture of the extended side wall with the slot delivery passage to an outboard juncture of the extended side wall with the common external surface of the stem;
- an angular side wall formed in the stem at the second side of the slot, having a first end spaced from the extended side wall and the transaxis plane; and
- the angular side wall extending from the first end thereof in a direction angularly away from the extended side wall and the transaxis plane to a second end of the angular side wall at a juncture with the common external surface of the stem.

17. The applicator as set forth in claim 16, which further comprises:
- the angular side wall and the extended side wall extending axially along at least a portion of the slot.

18. The applicator as set forth in claim 16, which further comprises:
- the angular side wall having a surface with a surface structure selected from the group of flat, peaks, undulations, concavity, and convexity.

* * * * *